US012336854B2

(12) United States Patent
Kawaguchi et al.

(10) Patent No.: US 12,336,854 B2
(45) Date of Patent: Jun. 24, 2025

(54) IMAGE PROCESSING DEVICE, METHOD PROGRAM AND SYSTEM FOR CHANGING A SIZE OF A RADIOGRAPHIC IMAGE ACCORDING TO A CORRECTION MAGNIFICATION

(71) Applicant: FUJIFILM CORPORATION, Tokyo (JP)

(72) Inventors: Kotatsu Kawaguchi, Kanagawa (JP); Tatsuya Taneichi, Kanagawa (JP); Naoyuki Nishino, Kanagawa (JP); Hisatsugu Horiuchi, Kanagawa (JP); Koji Taninai, Kanagawa (JP); Masayoshi Matsuura, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 336 days.

(21) Appl. No.: 17/954,341

(22) Filed: Sep. 28, 2022

(65) Prior Publication Data

US 2023/0107210 A1 Apr. 6, 2023

(30) Foreign Application Priority Data

Oct. 6, 2021 (JP) .................................. 2021-164920

(51) Int. Cl.
*G06T 3/40* (2024.01)
*A61B 6/00* (2006.01)
*A61B 6/50* (2024.01)

(52) U.S. Cl.
CPC ............ *A61B 6/5223* (2013.01); *A61B 6/505* (2013.01); *G06T 3/40* (2013.01)

(58) Field of Classification Search
CPC .................................. G06T 3/40; A61B 6/505

(Continued)

(56) References Cited

U.S. PATENT DOCUMENTS 5,008,947 A 4/1991 Yamada
6,459,772 B1 * 10/2002 Wiedenhoefer ........ G01B 15/00
378/207

(Continued)

FOREIGN PATENT DOCUMENTS

JP H02-104174 A 4/1990
JP 2004-154569 A 6/2004

(Continued)

OTHER PUBLICATIONS

English language translation of the following: Office action dated Apr. 1, 2025 from the JPO in a Japanese patent application No. 2021-164920 corresponding to the instant patent application. This office action translation is submitted now in order to supplement the understanding of the cited references which are being disclosed in the instant Information Disclosure Statement.

*Primary Examiner* — Jamares Q Washington
(74) *Attorney, Agent, or Firm* — SOLARIS Intellectual Property Group, PLLC

(57) ABSTRACT

An acquisition unit of an image processing device acquires a radiographic image which includes a patient and markers including lead plates and has been captured in a state in which the markers are disposed at a first position between a radiation source and the patient and a second position between a radiation detector and the patient, the subject being interposed between the first and second positions. An image processing unit calculates a correction magnification for setting a part of interest in the patient included in the radiographic image to a set dimension, on the basis of sizes of images of a plurality of the markers included in the radiographic image and an actual size of the markers, and changes a size of the radiographic image according to the correction magnification.

13 Claims, 16 Drawing Sheets

(58) Field of Classification Search
USPC .................................................. 382/132, 128
See application file for complete search history.

(56) References Cited

U.S. PATENT DOCUMENTS

| | | |
|---|---|---|
| 2004/0086082 A1 | 5/2004 | Foos et al. |
| 2010/0135467 A1 | 6/2010 | King et al. |
| 2012/0201354 A1 | 8/2012 | Kimura |
| 2014/0270067 A1* | 9/2014 | Clark .................... A61B 50/30 378/163 |
| 2015/0018671 A1 | 1/2015 | Marentis et al. |
| 2015/0379711 A1* | 12/2015 | Imai ......................... G06T 5/50 382/132 |
| 2017/0086777 A1 | 3/2017 | Kawamura |
| 2019/0046130 A1* | 2/2019 | Imamura ................ A61B 6/463 |

FOREIGN PATENT DOCUMENTS

| | | | |
|---|---|---|---|
| JP | 2005-192856 A | | 7/2005 |
| JP | 2009279295 A | * | 12/2009 |
| JP | 2012-161471 A | | 8/2012 |
| JP | 2014-207958 A | | 11/2014 |
| JP | 2017-060544 A | | 3/2017 |
| JP | 2019-033830 A | | 3/2019 |

* cited by examiner

FIG. 8

| ACTUAL INTERVAL BETWEEN LEAD PLATES | 20 mm |
|---|---|

| IMAGING MENU | COEFFICIENT |
|---|---|
| UPPER LIMBS, DECUBITUS POSITION, SIDE SPINE | 0.5 |
| UPPER LIMBS, DECUBITUS POSITION, SIDE SHOULDER (RADIATION SOURCE SIDE) | 0.55 |
| UPPER LIMBS, DECUBITUS POSITION, SIDE SHOULDER (RADIATION DETECTOR SIDE) | 0.45 |
| ⋮ | |
| LOWER LIMBS, DECUBITUS POSITION, SIDE PELVIS | 0.5 |
| LOWER LIMBS, DECUBITUS POSITION, SIDE KNEE (RADIATION SOURCE SIDE) | 0.525 |
| LOWER LIMBS, DECUBITUS POSITION, SIDE KNEE (RADIATION DETECTOR SIDE) | 0.475 |
| ⋮ | |

| SET DIMENSION | 1.0 (ACTUAL SIZE) |
|---|---|

— 63

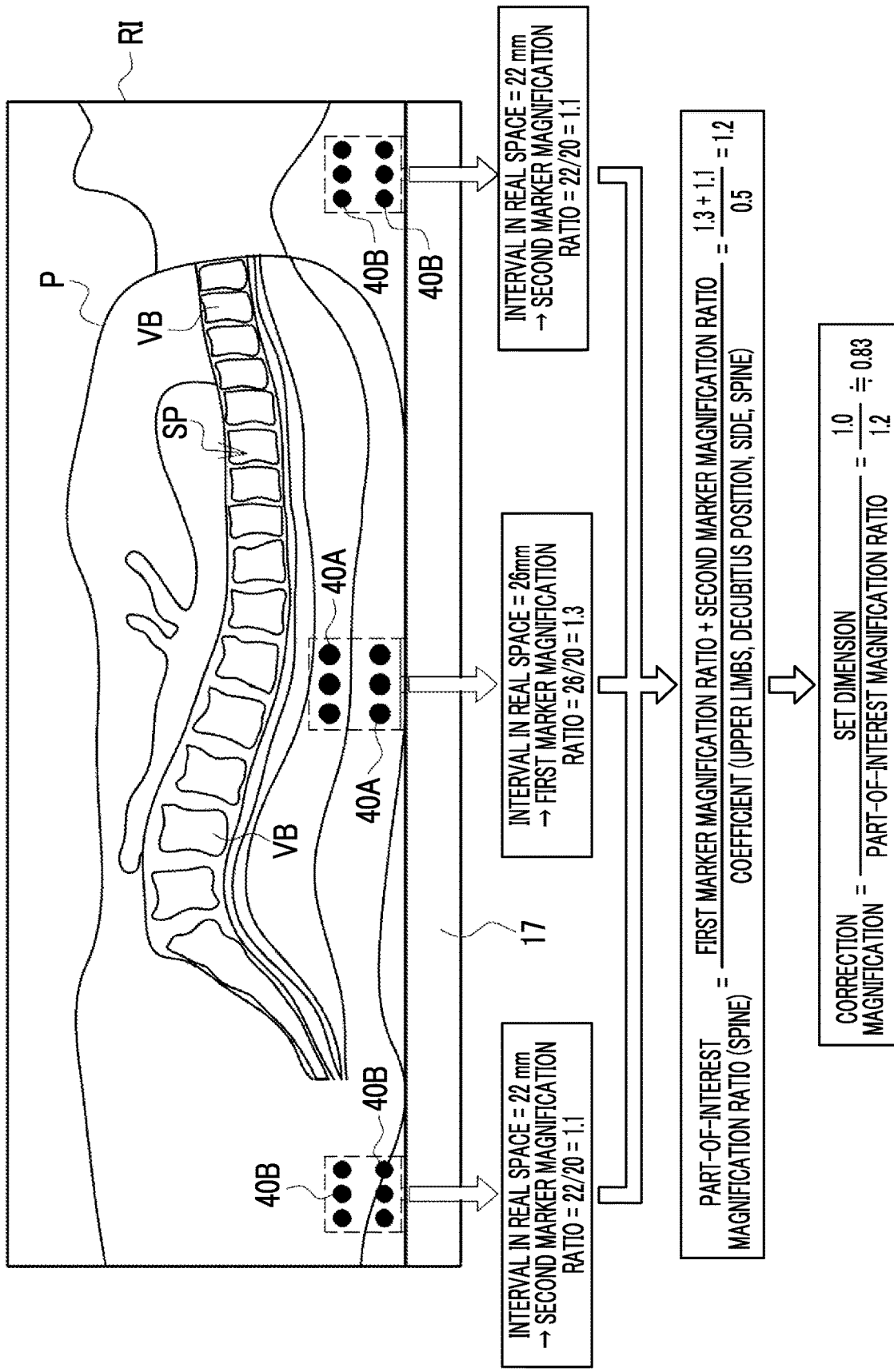

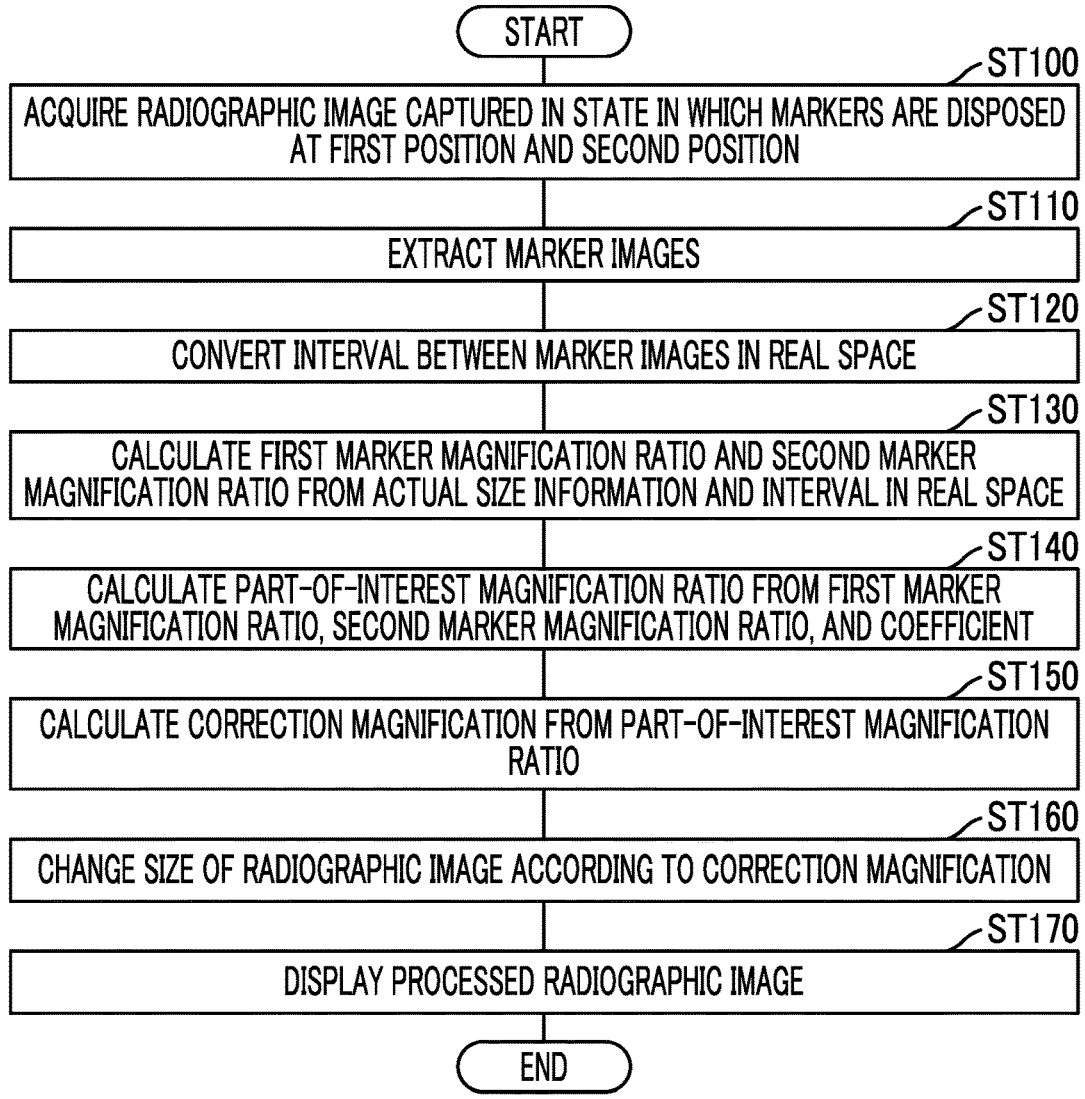
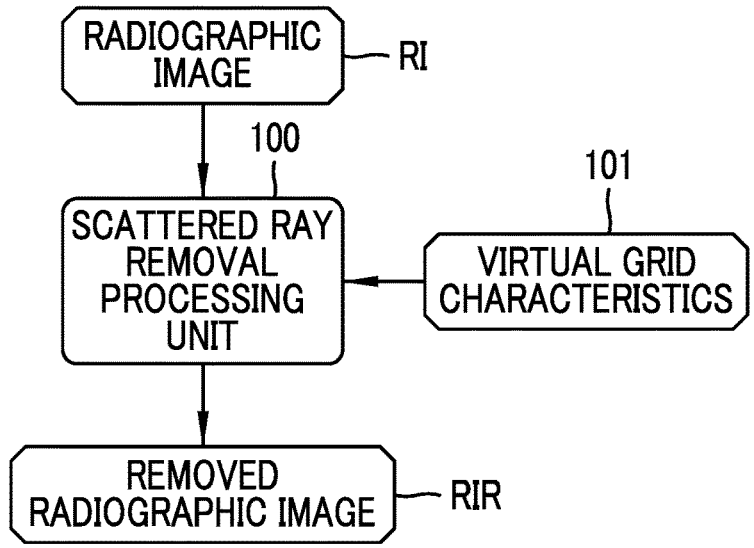

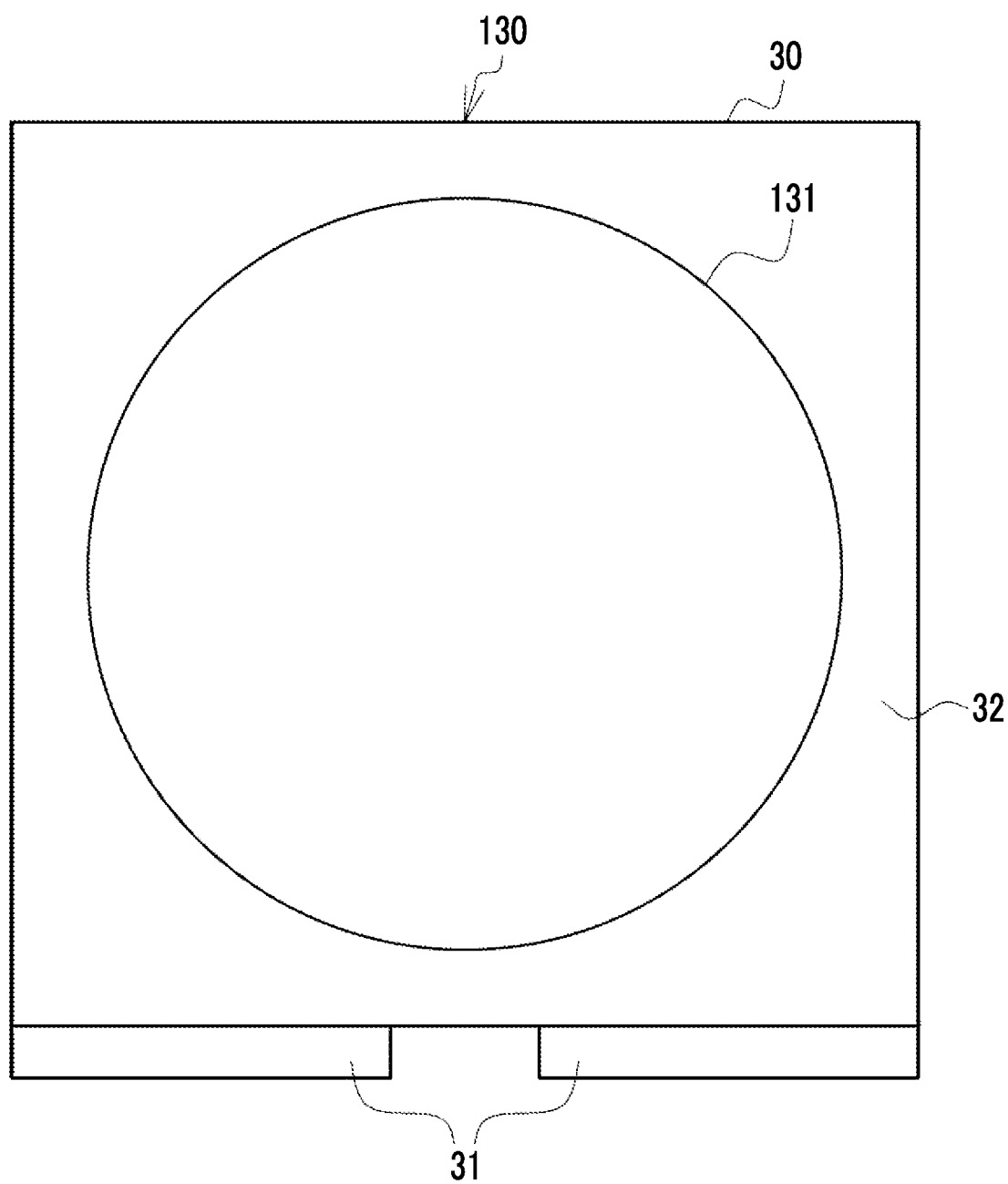

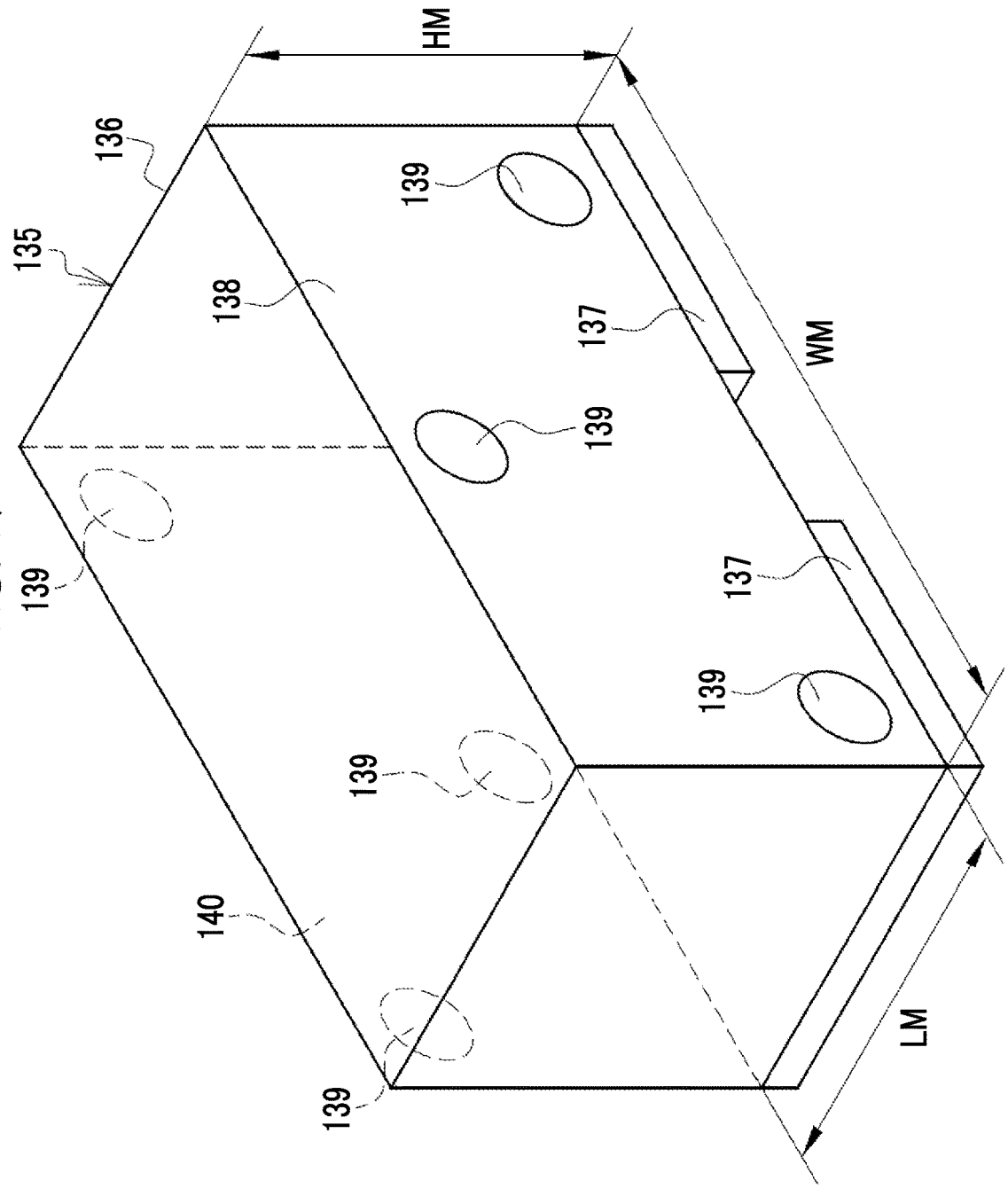

IMAGE PROCESSING DEVICE, METHOD PROGRAM AND SYSTEM FOR CHANGING A SIZE OF A RADIOGRAPHIC IMAGE ACCORDING TO A CORRECTION MAGNIFICATION

CROSS-REFERENCE TO RELATED APPLICATIONS

The present application claims priority under 35 U.S.C. § 119 to Japanese Patent Application No., 2021-164920 filed on Oct. 6, 2021. The above application is hereby expressly incorporated by reference, in its entirety, into the present application.

BACKGROUND

1. Technical Field

The technology of the present disclosure relates to an image processing device, a method for operating an image processing device, a program for operating an image processing device, and a radiography system.

2. Description of the Related Art

A radiography system is known which comprises a radiation source that irradiates a subject with radiation, a radiation detector that detects the radiation transmitted through the subject and outputs a radiographic image, and an image processing device that performs various types of image processing on the radiographic image. In this radiography system, in a case in which the radiation detector is disposed away from the subject, an image of the subject included in the radiographic image may be enlarged and may be different from a set dimension (for example, an actual size).

In a case in which the size of the image of the subject included in the radiographic image is different from the set dimension as described above, it may be difficult to observe the image. Therefore, JP2009-279295A discloses the following image processing device. That is, the image processing device disclosed in JP2009-279295A acquires a radiographic image, which includes a subject and a marker formed by a radiation attenuation member, and calculates a correction magnification for setting the subject to a set dimension on the basis of the image of the marker included in the radiographic image. Then, the image processing device changes the size of the radiographic image according to the correction magnification.

In JP2009-279295A, for example, one or two markers are disposed at positions on a surface of the radiation detector irradiated with radiation which are included in the radiographic image. Then, the correction magnification is calculated on the basis of the size of the image of one marker included in the radiographic image and the actual size of the marker, or an interval between the images of the two markers included in the radiographic image and the actual interval.

SUMMARY

In a case in which a radiographic image is observed, there are various parts of interest. For example, an observer wants to know the state of the spine of a subject. However, in JP2009-279295A, the correction magnification is calculated regardless of the part of interest. Therefore, in the radiographic image whose size has been changed, the part of interest may not have the set dimension.

An embodiment according to the technology of the present disclosure provides an image processing device, a method for operating an image processing device, a program for operating an image processing device, and a radiography system that can set a part of interest in a subject included in a radiographic image to a set dimension.

According to an aspect of the present disclosure, there is provided an image processing device comprising a processor. The processor acquires a radiographic image which includes a subject and markers including radiation attenuation members and has been captured in a state in which the markers are disposed at a first position between a radiation source and the subject and a second position between a radiation detector and the subject, the subject being interposed between the first and second positions, calculates a correction magnification for setting a part of interest in the subject included in the radiographic image to a set dimension, on the basis of sizes of images of a plurality of the markers included in the radiographic image and an actual size of the markers, and changes a size of the radiographic image according to the correction magnification.

Preferably, the processor acquires the radiographic image captured in a state in which a predetermined positional relationship is established between the first position and a position of the subject and between the second position and the position of the subject.

Preferably, the processor acquires the radiographic image captured in a state in which the first position and the second position are symmetric with respect to a central axis of the subject.

Preferably, the processor acquires the radiographic image captured in a state in which the plurality of markers are disposed at the second positions.

Preferably, the marker has a configuration in which a plurality of the radiation attenuation members are provided at predetermined intervals on a block-shaped main body that transmits radiation, and the processor calculates the correction magnification on the basis of an interval between images of the radiation attenuation members included in the radiographic image and an actual interval between the radiation attenuation members.

Preferably, the processor performs a scattered ray removal process corresponding to characteristics of a virtual grid on the radiographic image with reference to a pixel value based on radiation which has been attenuated by the radiation attenuation member and a pixel value based on radiation which has not been attenuated by the radiation attenuation member.

Preferably, the processor acquires the radiographic image obtained by imaging the subject in a decubitus position from a side.

Preferably, the processor acquires the radiographic image output from the radiation detector having a size that covers at least half of a body of the subject.

Preferably, the set dimension is an actual size.

Preferably, the part of interest is a spine.

According to another aspect of the present disclosure, there is provided a method for operating an image processing device. The method comprises: acquiring a radiographic image which includes a subject and markers including radiation attenuation members and has been captured in a state in which the markers are disposed at a first position between a radiation source and the subject and a second position between a radiation detector and the subject, the subject being interposed between the first and second positions; calculating a correction magnification for setting a part of interest in the subject included in the radiographic image to a set dimension, on the basis of sizes of images of a plurality of the markers included in the radiographic image and an actual size of the markers; and changing a size of the radiographic image according to the correction magnification.

According to still another aspect of the present disclosure, there is provided a program for operating an image processing device. The program causes a computer to execute a process comprising: acquiring a radiographic image which includes a subject and markers including radiation attenuation members and has been captured in a state in which the markers are disposed at a first position between a radiation source and the subject and a second position between a radiation detector and the subject, the subject being interposed between the first and second positions; calculating a correction magnification for setting a part of interest in the subject included in the radiographic image to a set dimension, on the basis of sizes of images of a plurality of the markers included in the radiographic image and an actual size of the markers; and changing a size of the radiographic image according to the correction magnification.

According to yet another aspect of the present disclosure, there is provided a radiography system comprising: a radiation source that irradiates a subject with radiation; a radiation detector that detects the radiation transmitted through the subject and outputs a radiographic image; markers that include radiation attenuation members and are disposed at a first position between the radiation source and the subject and a second position between the radiation detector and the subject, the first and second positions being included in the radiographic image, the subject being interposed between the first and second positions; and an image processing device that acquires the radiographic image, calculates a correction magnification for setting a part of interest in the subject included in the radiographic image to a set dimension, on the basis of sizes of images of a plurality of the markers included in the radiographic image and an actual size of the markers, and changes a size of the radiographic image according to the correction magnification.

According to the technology of the present disclosure, it is possible to provide an image processing device, a method for operating an image processing device, a program for operating an image processing device, and a radiography system that can set a part of interest in a subject included in a radiographic image to a set dimension.

BRIEF DESCRIPTION OF THE DRAWINGS

Exemplary embodiments according to the technique of the present disclosure will be described in detail based on the following figures, wherein:

FIG. 8 is a diagram illustrating actual size information;

FIG. 9 is a diagram illustrating a coefficient table;

FIG. 10 is a diagram illustrating set dimension information;

FIG. 12 is a diagram conceptually illustrating a processing of the image processing unit;

FIG. 13 is a flowchart illustrating a processing procedure of the image processing device;

FIG. 14 is a diagram illustrating a scattered ray removal processing unit;

FIG. 18 is a diagram illustrating yet another example of the marker; and

FIG. 19 is a diagram illustrating still yet another example of the marker.

DETAILED DESCRIPTION

First Embodiment

Figure 1:
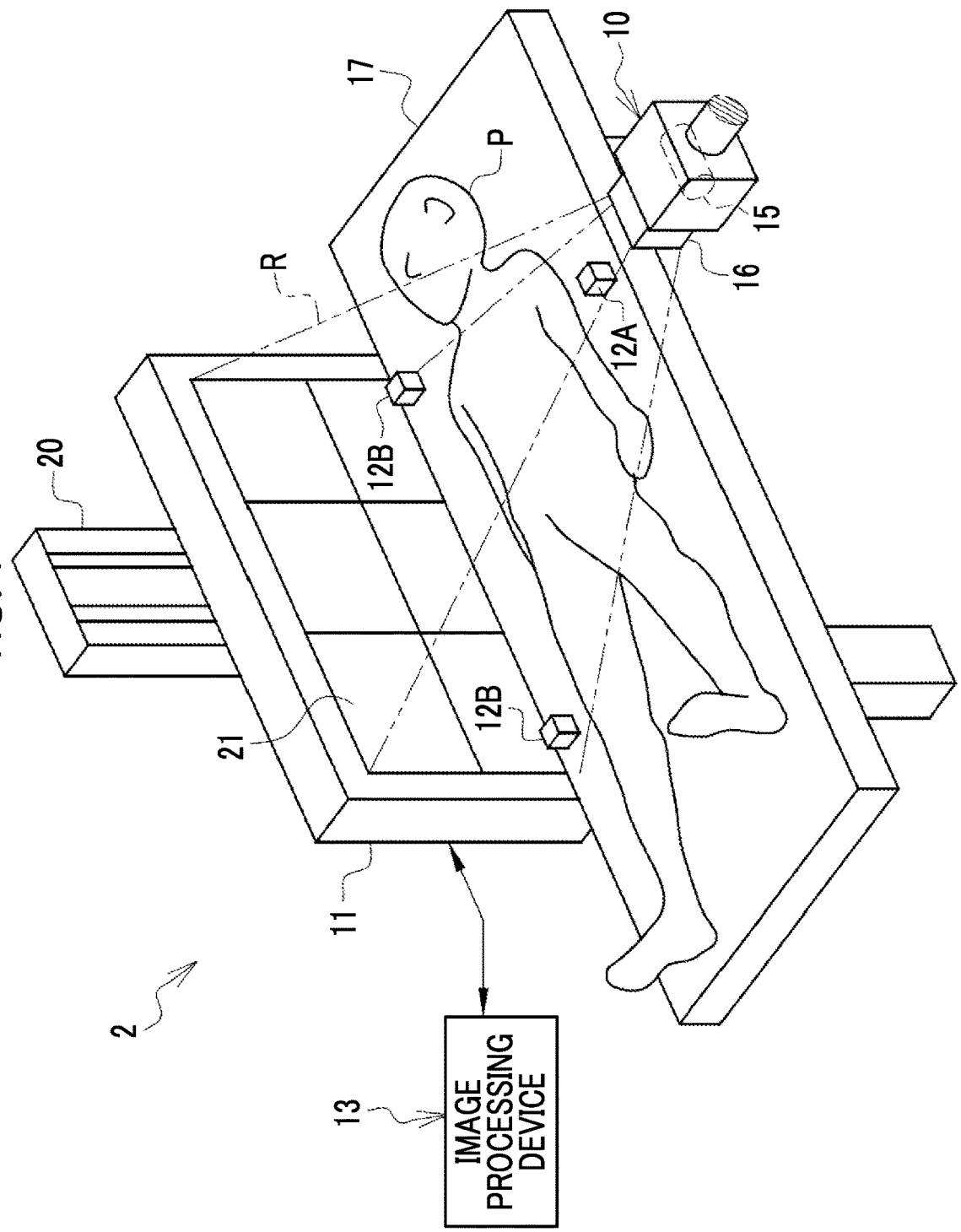
FIG. 1 is a perspective view illustrating a radiography system.
Figure 2:
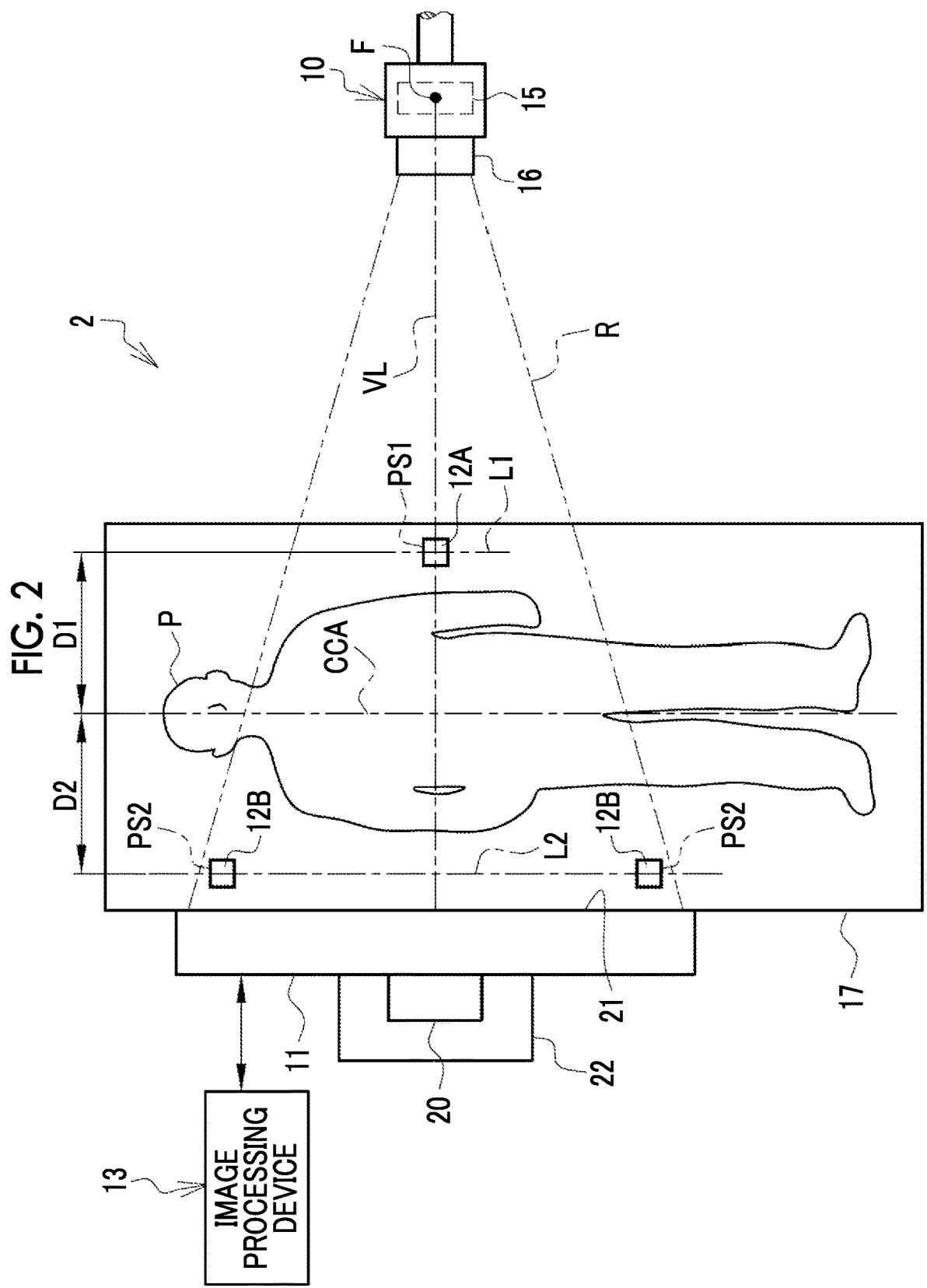
FIG. 2 is a top view illustrating the radiography system.

For example, as illustrated in FIGS. 1 and 2, a radiography system 2 comprises a radiation source 10, a radiation detector 11, a first marker 12A, a second marker 12B, and an image processing device 13.

The radiation source 10 has a radiation tube 15 that emits radiation R, such as X-rays or γ-rays, and an irradiation field limiter 16 that defines an irradiation field of the radiation R and emits the radiation R to a patient P who lies supine on a bed 17. FIGS. 1 and 2 illustrate an aspect in which the radiation R is emitted from the side of the upper limbs of the patient P in order to image a spine SP (see FIG. 5) of the patient P. The patient P is an example of a "subject" according to the technology of the present disclosure.

The radiation source 10 is a so-called portable radiation source that is mounted on a carriage to be movable and can change an irradiation position in an up-down direction and a left-right direction by an arm. A tube voltage and a tube current applied to the radiation tube 15 and the irradiation time of the radiation R, that is, irradiation conditions of the radiation R are input to an irradiation control device (not illustrated) by an operator of the radiography system 2 such as a radiology technician. In addition, instead of the tube current and the irradiation time, a tube current-irradiation time product may be input as the irradiation condition.

Figure 5:
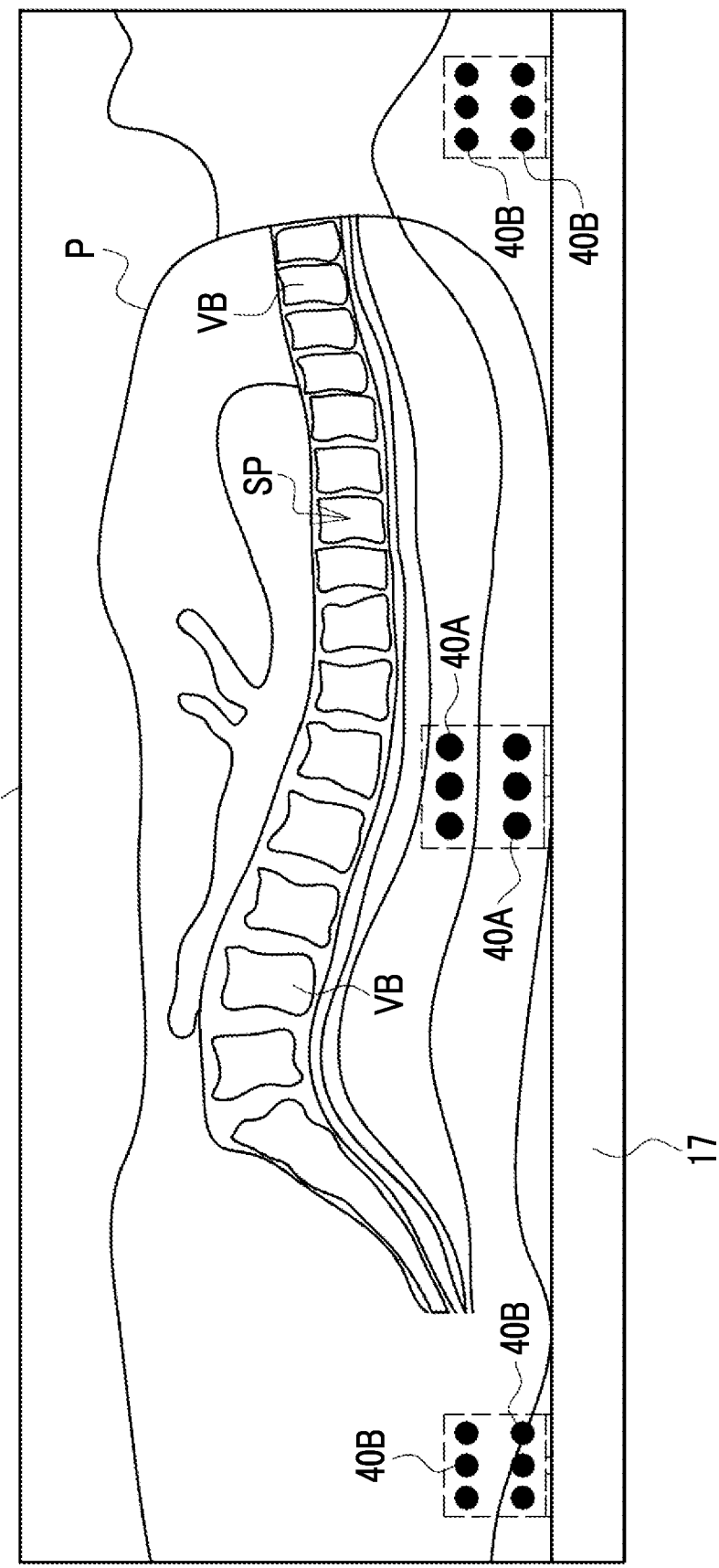
FIG. 5 is a diagram illustrating a radiographic image.

The radiation detector 11 includes a scintillator that converts the radiation R into visible light and a semiconductor substrate in which pixels that generate charge in response to the visible light are two-dimensionally arranged, detects the radiation R transmitted through the patient P, and outputs a radiographic image RI (see FIG. 5). Further, the radiation detector 11 may be a so-called direct conversion type including a semiconductor substrate in which pixels that generate charge in response to the radiation R are two-dimensionally arranged.

The radiation detector 11 has a function of detecting the start and end of the emission of the radiation R. In a case in which the start of the emission of the radiation R is detected, the radiation detector 11 starts an accumulation operation of accumulating charge in the pixels. In a case in which the end of the emission of the radiation R is detected, the radiation detector 11 ends the accumulation operation and starts a reading operation of reading the accumulated charge from the pixels.

The radiation detector 11 is attached to a support 20, can be moved up and down along the support 20, and can be rotated about an axis, which is parallel to a horizontal direction penetrating the support 20 in a front-rear direction, as a rotation axis. Further, the direction of the radiation detector 11 can be changed between a direction in which an irradiation surface 21 of the radiation R illustrated in FIGS. 1 and 2 is along the vertical direction and a direction (not illustrated) in which the irradiation surface 21 is along the horizontal direction. Furthermore, the radiation detector 11 can be moved by a carriage 22 that is disposed at a lower end of the support 20.

The radiation detector 11 has a size that covers half of the body of the patient P, for example, a size of 17 inches×49 inches. Therefore, it is possible to obtain the radiographic image RI including the upper limbs or the lower limbs of the patient P by one operation of emitting the radiation R.

The first marker 12A and the second marker 12B are used to calculate a correction magnification 93 (see FIG. 11) for setting a part of interest, here, the spine SP in the patient P included in the radiographic image RI to a set dimension. The number of first marker 12A is one, and the number of second markers 12B is two. The first marker 12A and the second marker 12B have the same configuration. Hereinafter, in a case in which the first marker 12A and the second marker 12B do not need to be distinguished from each other, they are collectively referred to as markers 12.

The markers 12 are disposed by the operator at positions on the bed 17 included in the radiographic image RI in the irradiation field of the radiation R prior to radiography. The first marker 12A is disposed at a first position PS1 between the radiation source 10 and the patient P, and the second marker 12B is disposed at a second position PS2 between the radiation detector 11 and the patient P. That is, the first marker 12A and the second marker 12B are disposed at positions having the patient P interposed therebetween.

The first position PS1 is a position that confronts the radiation source 10. Specifically, the first position PS1 is on a perpendicular line VL drawn from a focus F which is a generation point of the radiation R in the radiation tube 15 to the irradiation surface 21. The two second positions PS2 are positions on both sides of the irradiation surface 21 and are symmetric with respect to the perpendicular line VL.

A predetermined positional relationship is established between the first position PS1 and the position of the patient P and between the second position PS2 and the position of the patient P. Specifically, a distance D1 between a line L1, which passes through the first position PS1 and is parallel to the irradiation surface 21, and a cranio-caudal axis CCA of the patient P is equal to a distance D2 between a line L2, which passes through the second position PS2 and is parallel to the irradiation surface 21, and the cranio-caudal axis CCA of the patient P. Therefore, the first position PS1 and the second position PS2 are symmetric with respect to the cranio-caudal axis CCA of the patient P. The cranio-caudal axis CCA is an example of a "central axis" according to the technology of the present disclosure.

Here, for example, the "equal" distance, the "confronting" position, and the "symmetric" position include errors that are generally allowed in the technical field to which the technology of the present disclosure belong, in addition to exactly "equal", directly "confronting", and perfectly "symmetric", and indicate "equal", "confronting", and "symmetric" in the sense of including an error (for example, an error of about 1% to 10%) that does not contradict the purpose of the technology of the present disclosure. Therefore, for the first position PS1 and the second position PS2, an error of, for example, about 50 mm to 60 mm is allowed.

Figure 3:
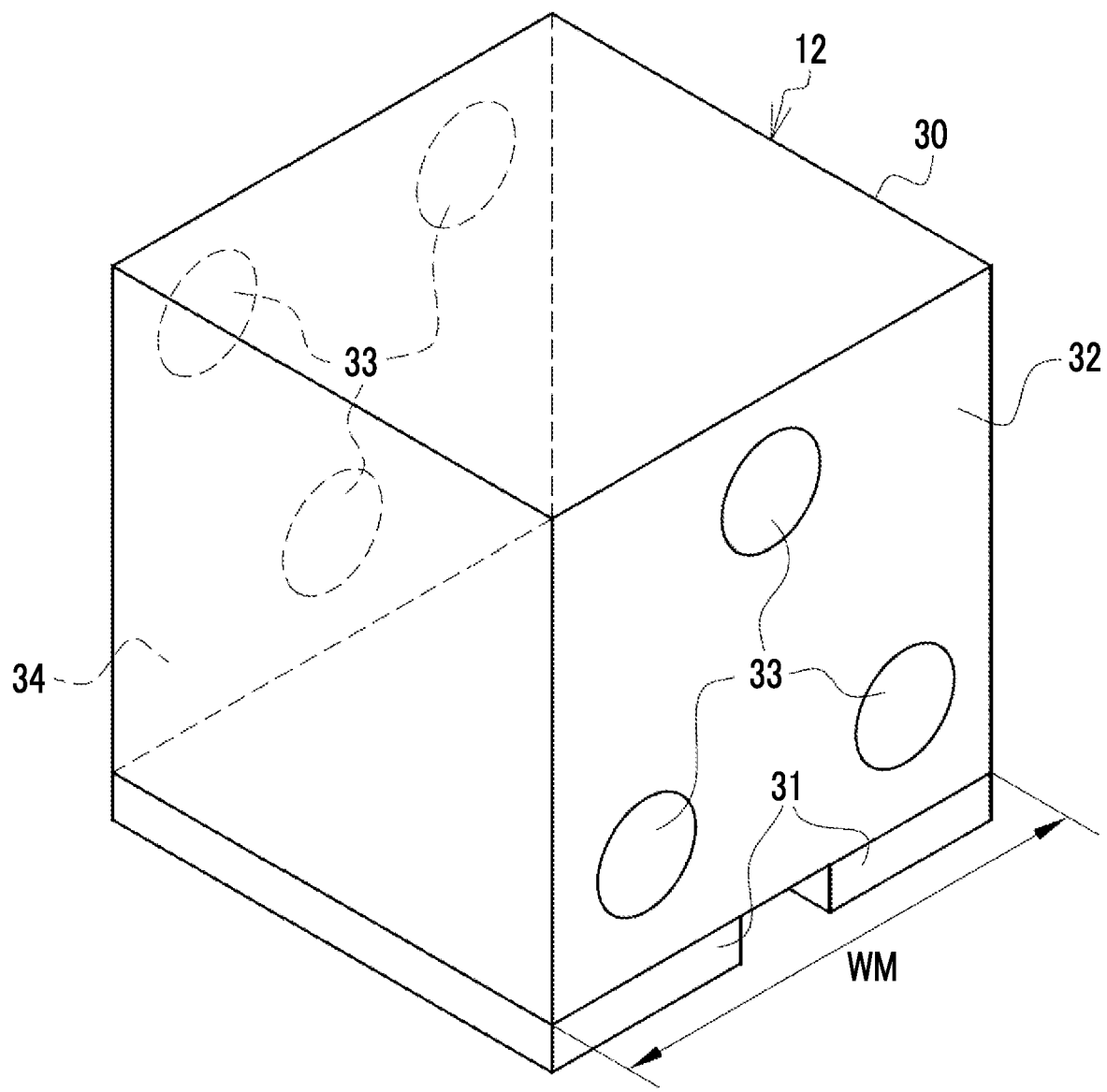
FIG. 3 is a perspective view illustrating a marker.
Figure 4:
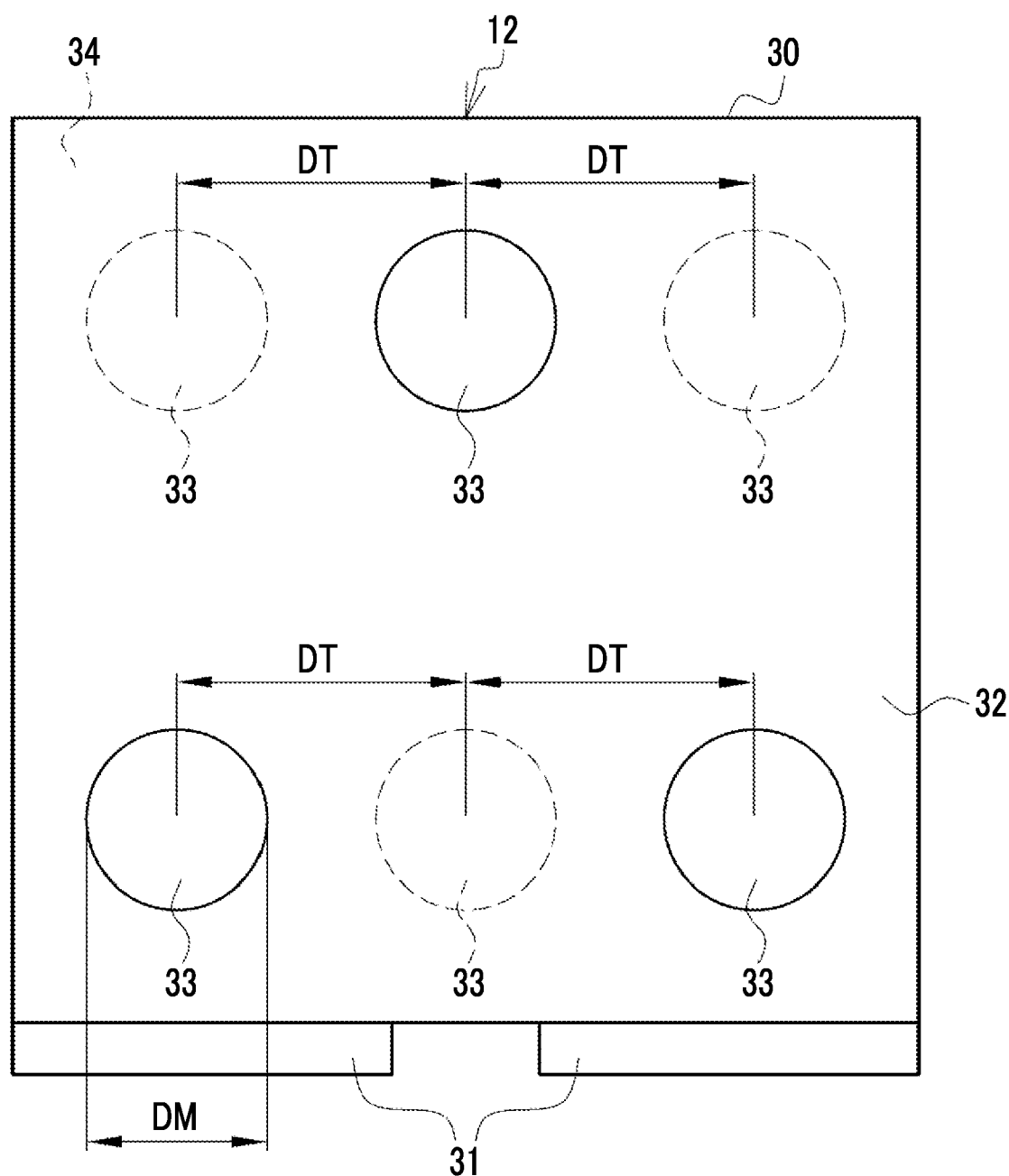
FIG. 4 is a front view illustrating the marker.

For example, as illustrated in FIGS. 3 and 4, the marker 12 is composed of a main body 30 and a pedestal 31 that is attached to a bottom of the main body 30. The marker 12 is placed with the pedestal 31 facing down. The main body 30 is a cube having a side length (width) WM of, for example, 50 mm. The main body 30 and the pedestal 31 are made of a material that transmits the radiation R, such as, carbon fiber reinforced plastic (CFRP).

Three lead plates 33 are attached to a front surface 32 of the main body 30. Three lead plates 33 are also attached to a rear surface 34 of the main body 30 which is opposite to the front surface 32. The lead plate 33 has a circular shape with a diameter DM of, for example, about 6 to 7 mm. The lead plate 33 is an example of a "radiation attenuation member" according to the technology of the present disclosure.

The three lead plates 33 are disposed at the positions of the vertices of a regular triangle on each of the front surface 32 and the rear surface 34. The disposition of the lead plates 33 attached to the front surface 32 is 180° different from the disposition of the lead plates 33 attached to the rear surface 34.

In a case in which the marker 12 is viewed from the front surface 32, the lead plates 33 are arranged in two rows and three columns as illustrated in FIG. 4. The lead plates 33 adjacent to each other in the horizontal direction have a predetermined interval DT. The interval DT is, for example, 20 mm.

For example, as illustrated in FIG. 5, the radiographic image RI captured in the state illustrated in FIGS. 1 and 2 includes an image of patient P and an image of the spine SP mainly composed of a plurality of vertebrae VB. Further, the radiographic image RI includes images (hereinafter, referred to as first marker images) 40A of the lead plates 33 of the first marker 12A and images (hereinafter, referred to as second marker images) 40B of the lead plates 33 of the second marker 12B. Since the first marker 12A is disposed at the first position PS1 that is farther from the radiation detector 11 than the second marker 12B, the first marker image 40A is slightly larger than the second marker image 40B in the radiographic image RI. Hereinafter, in a case in which the first marker image 40A and the second marker image 40B do not need to be distinguished from each other, they are collectively referred to as marker images 40.

The image processing device 13 is, for example, a notebook personal computer or a tablet terminal. The image processing device 13 is connected to the radiation detector 11 in a wired manner or wirelessly and receives the radiographic image RI from the radiation detector 11. The image processing device 13 performs various types of image processing on the radiographic image RI from the radiation detector 11.

Figure 6:
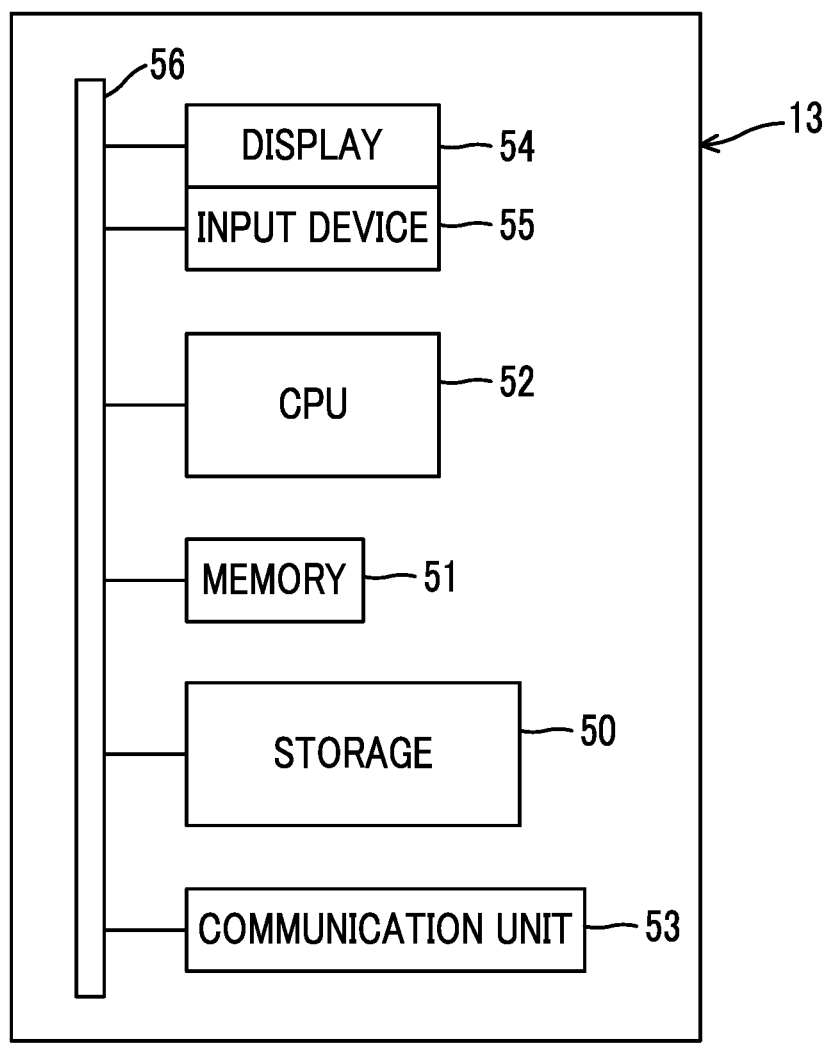
FIG. 6 is a block diagram illustrating a computer constituting an image processing device.

For example, as illustrated in FIG. 6, a computer constituting the image processing device 13 comprises a storage 50, a memory 51, a central processing unit (CPU) 52, a communication unit 53, a display 54, and an input device 55. These units are connected to each other through a bus line 56.

The storage 50 is a hard disk drive that is provided in the computer constituting the image processing device 13 or is connected to the computer through a cable or a network. Alternatively, the storage 50 is a disk array in which a plurality of hard disk drives are connected. The storage 50 stores, for example, a control program, such as an operating system, various application programs, and various kinds of data associated with these programs. In addition, a solid state drive may be used instead of the hard disk drive.

The memory 51 is a work memory used by the CPU 52 to perform processes. The CPU 52 loads the program stored in the storage 50 to the memory 51 and performs a process corresponding to the program. Therefore, the CPU 52 controls the overall operation of each unit of the computer. The CPU 52 is an example of a "processor" according to the technology of the present disclosure. In addition, the memory 51 may be provided in the CPU 52.

The communication unit 53 controls the transmission of various kinds of information to an external device such as the radiation detector 11. The display 54 displays various screens. The various screens have operation functions by a graphical user interface (GUI). The computer constituting the image processing device 13 receives operation instructions input from the input device 55 through various screens. The input device 55 is, for example, a keyboard, a mouse, a touch panel, and a microphone for voice input.

Figure 7:
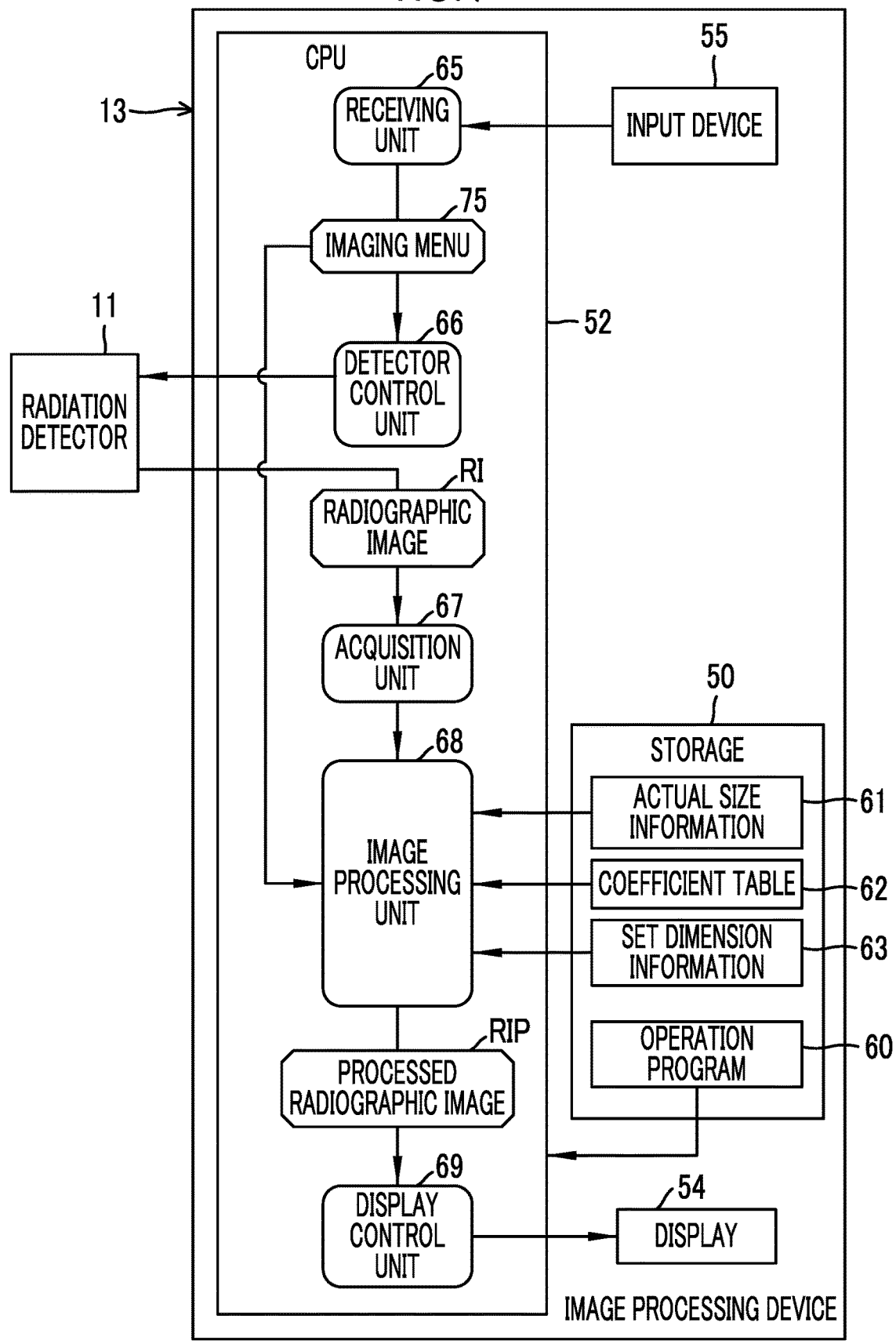
FIG. 7 is a block diagram illustrating a processing unit of a CPU of the image processing device.

For example, as illustrated in FIG. 7, an operation program 60 is stored in the storage 50 of the image processing device 13. The operation program 60 is an application program for causing the computer to function as the image processing device 13. That is, the operation program 60 is an example of a "program for operating an image processing device" according to the technology of the present disclosure. The storage 50 also stores actual size information 61, a coefficient table 62, and set dimension information 63.

In a case in which the operation program 60 is started, the CPU 52 of the computer constituting the image processing device 13 functions as a receiving unit 65, a detector control unit 66, an acquisition unit 67, an image processing unit 68, and a display control unit 69 in cooperation with, for example, the memory 51.

The receiving unit 65 receives the setting of an imaging menu 75 by the operator through the input device 55. The imaging menu 75 is a set of rough imaging parts, such as the upper limbs and the lower limbs, the body positions of the patient P, such as a standing position, a decubitus position, and a sitting position, the incident directions of the radiation R on the patient P, such as the front, the rear, and the side, and the part of interest (see FIG. 9). The receiving unit 65 outputs the imaging menu 75 to the detector control unit 66 and the image processing unit 68.

The detector control unit 66 controls the operation of the radiation detector 11 according to the imaging menu 75. For example, the detector control unit 66 transmits a gain set value corresponding to the imaging menu 75 to the radiation detector 11. The radiation detector 11 amplifies a pixel value of the radiographic image RI with the transmitted gain set value.

The acquisition unit 67 acquires the radiographic image RI from the radiation detector 11. As illustrated in FIG. 5, the radiographic image RI includes the image of the patient P, the first marker image 40A of the first marker 12A disposed at the first position PS1, and the second marker image 40B of the second marker 12B disposed at the second position PS2. The acquisition unit 67 outputs the radiographic image RI to the image processing unit 68.

The image processing unit 68 performs various types of image processing on the radiographic image RI to obtain a processed radiographic image RIP. The various types of image processing include a process of changing the size of the radiographic image RI on the basis of the actual size information 61, the coefficient table 62, and the set dimension information 63. The image processing unit 68 outputs the processed radiographic image RIP to the display control unit 69.

The display control unit 69 controls the display of various screens on the display 54. For example, the display control unit 69 displays a screen including the processed radiographic image RIP on the display 54.

For example, as illustrated in FIG. 8, an actual interval DT between the adjacent lead plates 33 illustrated in FIG. 4 is registered in the actual size information 61. In this example, 20 mm is registered.

For example, as illustrated in FIG. 9, coefficients are registered for each imaging menu 75 in the coefficient table 62. For example, a coefficient of 0.5 is registered in the imaging menu 75 corresponding to the upper limbs, the decubitus position, and the side in a case in which the part of interest is the spine, which is illustrated in FIGS. 1 and 2. Further, a coefficient of 0.55 is registered in the imaging menu 75 corresponding to the upper limbs, the decubitus position, and the side in a case in which the part of interest is the shoulder on the side of the radiation source 10. Further, a coefficient of 0.475 is registered in the imaging menu 75 corresponding to the upper limbs, the decubitus position, and the side in a case in which the part of interest is the knee on the side of the radiation detector 11. A value based on that the first position PS1 and the second position PS2 are symmetric with respect to the cranio-caudal axis CCA of the patient P is set as the coefficient.

For example, as illustrated in FIG. 10, the set dimension of the part of interest is registered in the set dimension information 63. In this example, 1.0, that is, the actual size is registered.

Figure 11:
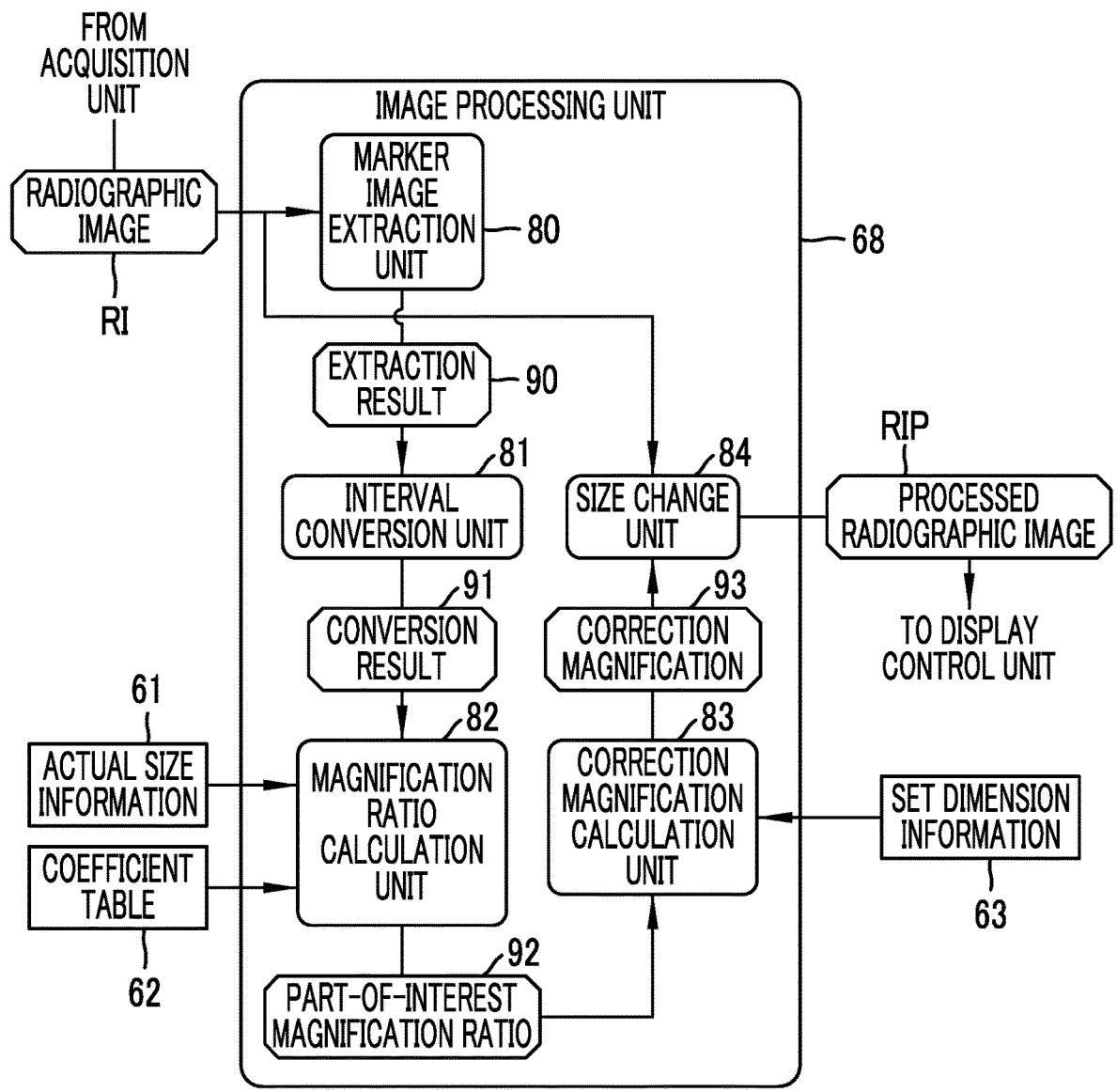
FIG. 11 is a diagram illustrating a detailed configuration of an image processing unit.

For example, as illustrated in FIG. 11, the image processing unit 68 includes a marker image extraction unit 80, an interval conversion unit 81, a magnification ratio calculation unit 82, a correction magnification calculation unit 83, and a size change unit 84. In addition to these units, the image processing unit 68 includes, for example, an offset correction unit, a sensitivity correction unit, a defective pixel correction unit.

The marker image extraction unit 80 extracts the images of the circular lead plates 33, that is, the marker images 40 included in the radiographic image RI from the acquisition unit 67, using a well-known pattern recognition technique. The marker image extraction unit 80 outputs an extraction result 90 of the marker images 40 to the interval conversion unit 81. Specifically, the extraction result 90 is the coordinates of the positions of the centers of the marker images 40.

The interval conversion unit 81 converts an interval between the pixels of adjacent marker images 40 represented by the extraction result 90 into an interval in the real space. Specifically, in a case in which the interval between the pixels of the adjacent marker images 40 represented by the extraction result 90 is dx [pixels] and the size of the pixel is p [μm], the interval DX [mm] in the real space is calculated by the following Expression (1).

$$DX = dx \times p \times 10^{-3} \quad (1)$$

For example, in a case in which the interval dx between the pixels is 110 pixels and the size p of the pixel is 200 μm, the interval DX in the real space is DX=110×0.2=22 mm.

Here, there are six marker images 40 obtained by one marker 12, and there are four intervals between the pixels of adjacent marker images 40. Therefore, the interval DX between the marker images 40 in the real space is calculated in four ways. The interval conversion unit 81 outputs a representative value, such as the average value or the maximum value of the intervals DX between the four marker images 40 in the real space, as the conversion result 91 to the magnification ratio calculation unit 82.

The magnification ratio calculation unit 82 calculates a part-of-interest magnification ratio 92 on the basis of the actual size information 61, the coefficient table 62, and the conversion result 91. The part-of-interest magnification ratio 92 indicates the magnification ratio of the part of interest in the radiographic image RI. The magnification ratio calculation unit 82 outputs the part-of-interest magnification ratio 92 to the correction magnification calculation unit 83.

The correction magnification calculation unit 83 calculates a correction magnification 93 on the basis of the set dimension information 63 and the part-of-interest magnification ratio 92. The correction magnification calculation unit 83 outputs the correction magnification 93 to the size change unit 84.

The size change unit 84 changes the size of the radiographic image RI according to the correction magnification 93 to obtain the processed radiographic image RIP.

FIG. 12 conceptually illustrates the process of the image processing unit 68. FIG. 12 illustrates a case in which the interval conversion unit 81 performs conversion such that the interval DX between the first marker images 40A in the real space is 26 mm and the interval DX between the second marker images 40B in the real space is 22 mm.

First, the magnification ratio calculation unit 82 divides the interval DX in the real space by the actual interval DT between the adjacent lead plates 33 registered in the actual size information 61 to calculate the magnification ratio of the marker 12. In this example, since the interval DX between the first marker images 40A in the real space is 26 mm and the actual interval DT between the lead plates 33 is 20 mm, the magnification ratio (hereinafter, referred to as a first marker magnification ratio) of the first marker 12A is 26/20=1.3. Further, since the interval DX between the second marker images 40B in the real space is 22 mm, the magnification ratio (hereinafter, referred to as a second marker magnification ratio) of the second marker 12B is 22/20=1.1.

The magnification ratio calculation unit 82 adds the first marker magnification ratio and the second marker magnification ratio and divides the added value by a coefficient to calculate the part-of-interest magnification ratio 92. In this example, the imaging menu 75 is "the upper limbs, the decubitus position, and the spine", and the coefficient corresponding to the imaging menu 75 is 0.5 according to the coefficient table 62 illustrated in FIG. 9. Therefore, the part-of-interest magnification ratio 92 is (1.3+1.1)/0.5=1.2.

The correction magnification calculation unit 83 divides the set dimension registered in the set dimension information 63 by the part-of-interest magnification ratio 92 to calculate the correction magnification 93. In this example, the set dimension is 1.0 which is the actual size. Therefore, the correction magnification 93 is 1.0/1.2≈0.83. In this case, the size change unit 84 reduces the radiographic image RI from the acquisition unit 67 to 0.83 times of the original size to obtain the processed radiographic image RIP.

Next, the operation of the above-mentioned configuration will be described with reference to a flowchart illustrated in FIG. 13. First, in a case in which the operation program 60 is started in the image processing device 13, the CPU 52 of the image processing device 13 functions as the receiving unit 65, the detector control unit 66, the acquisition unit 67, the image processing unit 68, and the display control unit 69 as illustrated in FIG. 7. As illustrated in FIG. 11, the image processing unit 68 functions as the marker image extraction unit 80, the interval conversion unit 81, the magnification ratio calculation unit 82, the correction magnification calculation unit 83, and the size change unit 84.

The operator operates the input device 55 to input the imaging menu 75. The imaging menu 75 is received by the receiving unit 65 and is output from the receiving unit 65 to the detector control unit 66 and the image processing unit 68.

Further, the operator sets the irradiation conditions of the radiation R corresponding to the imaging menu 75 in an irradiation control device (not illustrated). Then, the radiation source 10, the radiation detector 11, the marker 12, and the patient P are disposed at, for example, the positions illustrated in FIGS. 1 and 2. After the disposition, the operator operates the radiation source 10 to irradiate the patient P with the radiation R from the radiation source 10.

Here, the markers 12 may be disposed after the patient P is positioned, or the patient P may be positioned after the markers 12 are disposed. In any case, there is no change in the disposition of the markers 12 at the first position PS1 between the radiation source 10 and the patient P and at the second position PS2 between the radiation detector 11 and the patient P.

The radiation detector 11 detects the radiation R (visible light converted from the radiation R) transmitted through the patient P under the control of the detector control unit 66. Then, the radiographic image RI is output from the radiation detector 11.

For example, as illustrated in FIG. 13, the acquisition unit 67 acquires the radiographic image RI from the radiation detector 11 (Step ST100). The radiographic image RI is an image captured in a state in which the first marker 12A and the second marker 12B are disposed at the first position PS1 and the second position PS2 having the patient P interposed therebetween. The radiographic image RI is output from the acquisition unit 67 to the image processing unit 68.

In the image processing unit 68, the marker image extraction unit 80 extracts the marker images 40 included in the radiographic image RI (Step ST110). The extraction result 90 of the marker images 40 is output from the marker image extraction unit 80 to the interval conversion unit 81.

Next, the interval conversion unit 81 converts the interval dx between the pixels of adjacent marker images 40 represented by the extraction result 90 into the interval DX in the real space (Step ST120). The conversion result 91 including the interval DX in the real space is output from the interval conversion unit 81 to the magnification ratio calculation unit 82.

The magnification ratio calculation unit 82 calculates the first marker magnification ratio and the second marker magnification ratio from the actual size information 61 and the interval DX in the real space as illustrated in FIG. 12 (Step ST130). Then, the part-of-interest magnification ratio 92 is calculated from the first marker magnification ratio, the second marker magnification ratio, and the coefficients registered in the coefficient table 62 (Step ST140). The part-of-interest magnification ratio 92 is output from the magnification ratio calculation unit 82 to the correction magnification calculation unit 83.

The correction magnification calculation unit 83 calculates the correction magnification 93 from the part-of-interest magnification ratio 92 (Step ST150). The correction magnification 93 is output from the correction magnification calculation unit 83 to the size change unit 84.

The size change unit 84 changes the size of the radiographic image RI from the acquisition unit 67 according to the correction magnification 93 to obtain the processed radiographic image RIP (Step ST160). The processed radiographic image RIP is output from the size change unit 84 (image processing unit 68) to the display control unit 69.

A screen including the processed radiographic image RIP is displayed on the display 54 under the control of the display control unit 69 (Step ST170). The operator observes the processed radiographic image RIP displayed on the display 54.

As described above, the image processing device 13 comprises the acquisition unit 67 and the image processing unit 68. The acquisition unit 67 acquires the radiographic image RI which includes the patient P and the markers 12 including the lead plates 33 and is captured in a state in which the markers 12 are disposed at the first position PS1 between the radiation source 10 and the patient P and at the second position PS2 between the radiation detector 11 and the patient P. The image processing unit 68 calculates the correction magnification 93 for setting the part of interest in the patient P included in the radiographic image RI to the set dimensions on the basis of the sizes (the interval DX between the marker images 40 in the real space) of the images (the marker images 40 which are the images of the lead plates 33) of a plurality of markers and the actual size (the actual interval DT between adjacent lead plates 33) of the markers 12 and changes the size of the radiographic image RI according to the correction magnification 93. Therefore, it is possible to set the part of interest in the patient P included in the radiographic image RI to the set dimension.

As illustrated in FIG. 2, the radiographic image RI is captured in a state in which a predetermined positional relationship is established between the first position PS1 and the position of the patient P and between the second position PS2 and the position of the patient P. Specifically, the radiographic image RI is captured in a state in which the first position PS1 and the second position PS2 are symmetric with respect to the cranio-caudal axis CCA of the patient P. Therefore, it is possible to easily calculate the correction magnification 93 for setting the part of interest to the set dimension, using the coefficient set as the value based on this state.

At the second position PS2, the second marker image 40B is unclear since the patient P is present in front of the second position PS2, and there is a concern that the marker image extraction unit 80 will not extract the second marker image 40B. Therefore, in the technology of the present disclosure, as illustrated in FIG. 2, two second markers 12B are disposed at the second positions PS2. As a result, it is possible to reduce the concern that the marker image extraction unit 80 will not extract the second marker image 40B. In addition, the number of second markers 12B disposed at the second positions PS2 is not limited to two and may be one or three or more.

As illustrated in FIGS. 3 and 4, the marker 12 has the configuration in which six lead plates 33 are provided in the block-shaped main body 30 that transmits the radiation R at the predetermined interval DT. As illustrated in FIG. 12, the image processing unit 68 calculates the correction magnification 93 on the basis of the interval DX between the marker images 40 included in the radiographic image RI and the actual interval DT of the marker 12. Therefore, it is possible to calculate the correction magnification 93 with higher accuracy.

As illustrated in FIG. 5, the radiographic image RI is an image obtained by imaging the patient P in the decubitus position from the side. In a case in which the patient P in the decubitus position is imaged from the side, the image of the patient P in the radiographic image RI is further enlarged since there is a relatively long distance (about 500 mm to 600 mm) between the radiation detector 11 and the patient P, as illustrated in FIGS. 1 and 2. Therefore, it is particularly necessary to set the part of interest in the patient P included in the radiographic image RI to the set dimension. Therefore, it is possible to further exert the effect of the technology of the present disclosure that the part of interest in the patient P included in the radiographic image RI can be set to the set dimension. In addition, the radiographic image RI is not limited to the image obtained by imaging the patient P in the decubitus position from the side and may be, for example, an image obtained by imaging the patient P in the sitting position from the front.

As illustrated in FIGS. 1 and 2, the radiation detector 11 has a size that covers at least half of the body of the patient P. Therefore, it is necessary to keep the distance between the radiation source 10 and the patient P to some extent (about 1400 mm to 1500 mm), and the image of the patient P in the radiographic image RI is further enlarged. Therefore, as in the case in which the patient P in the decubitus position is imaged from the side, it is particularly necessary to set the part of interest in the patient P included in the radiographic image RI to the set dimension, and it is possible to further exert the effect of the technology of the present disclosure that the part of interest in the patient P included in the radiographic image RI can be set to the set dimension. In addition, the radiation detector 11 may not have a size that covers half of the body of the patient P. For example, the radiation detector 11 may have a size of 17 inches×17 inches.

As illustrated in FIG. 10, the set dimension is the actual size. Therefore, the processed radiographic image RIP is an image that makes it easy for the operator to intuitively understand the size of the part of interest and makes it easy to smoothly progress a diagnosis on the part of interest. In addition, the set dimension is not limited to the actual size and may be, for example, 1.2 times or 0.8 times. The set dimension may be changed for each medical facility or may be freely set by the operator.

As illustrated in, for example, FIG. 5, the part of interest is the spine SP. The spine SP is subjected to a relatively delicate orthopedic surgery of drilling a hole in a particular vertebra VB. Therefore, as in the case in which the patient P in the decubitus position is imaged from the side, it is particularly necessary to set the part of interest in the patient P included in the radiographic image RI to the set dimension, and it is possible to further exert the effect of the technology of the present disclosure that the part of interest in the patient P included in the radiographic image RI can be set to the set dimension. In addition, the part of interest is not limited to the spine. As illustrated in FIG. 9, the part of interest may be, for example, the shoulder, the pelvis, or the knee.

Second Embodiment

For example, as illustrated in FIG. 14, an image processing unit according to a second embodiment functions as a scattered ray removal processing unit 100 in addition to the processing units 80 to 84 according to the first embodiment. The scattered ray removal processing unit 100 performs a scattered ray removal process corresponding to characteristics 101 of a virtual grid (hereinafter, referred to as virtual grid characteristics) on the radiographic image RI to convert the radiographic image RI into a removed radiographic image RIR.

The virtual grid characteristics 101 are input by the operator through the input device 55. Specifically, the virtual grid characteristics 101 are the scattered ray transmittance and primary ray (also referred to as direct ray) transmittance of the virtual grid. The scattered ray transmittance is close to 0, and the primary ray transmittance is close to 1.

Figure 15:
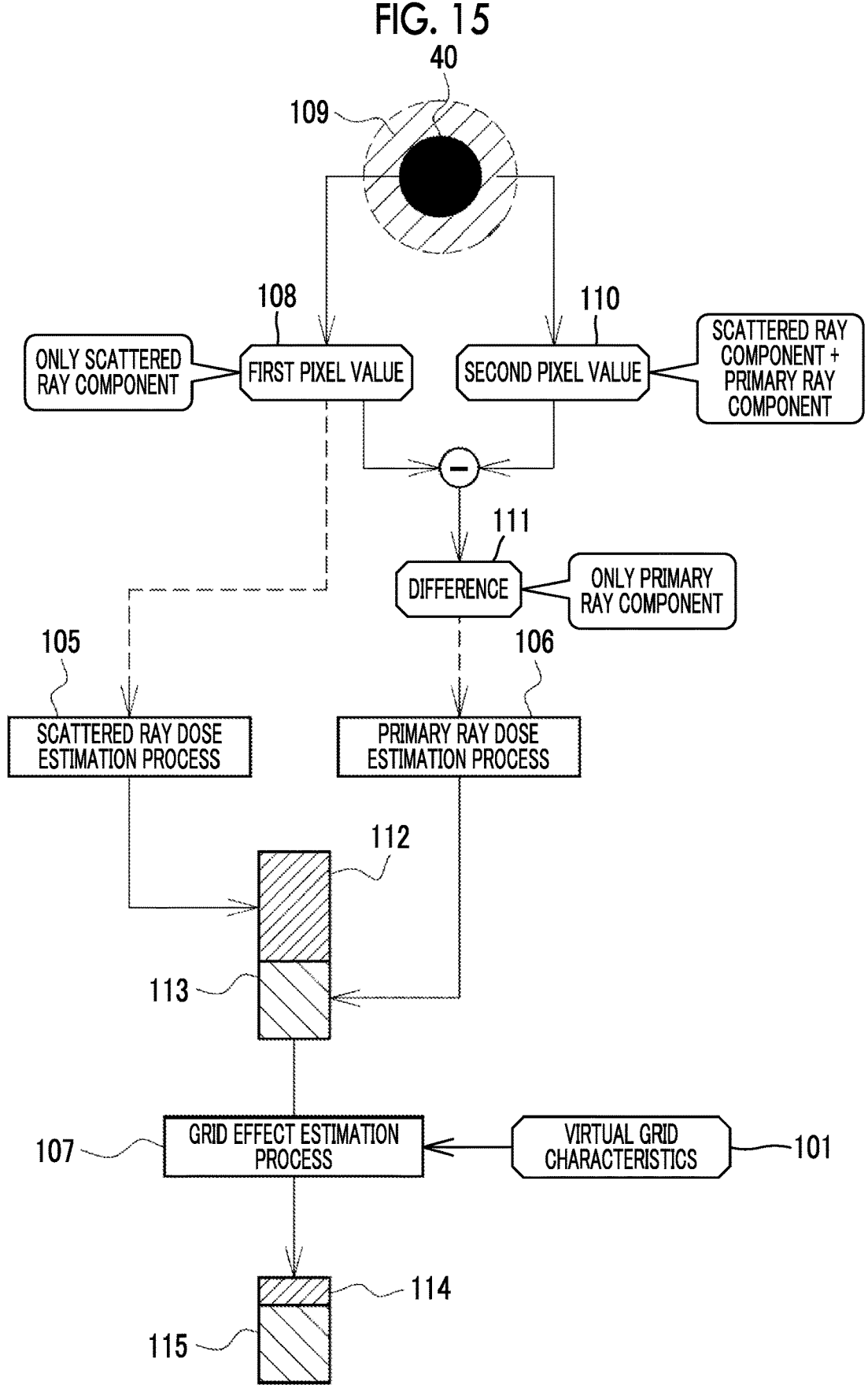
FIG. 15 is a diagram conceptually illustrating a processing of the scattered ray removal processing unit.

The scattered ray removal process is, for example, a technique that achieves the same image quality improvement effect as that in a case in which a grid is used, using image processing, without actually using the grid, as described in JP6006193B. For example, as illustrated in FIG. 15, in the scattered ray removal process, a scattered ray dose estimation process 105, a primary ray dose estimation process 106, and a grid effect estimation process 107 are performed. The scattered ray dose estimation process 105 is a process of estimating a scattered ray dose in the radiation R, which reaches the irradiation surface 21 of the radiation detector 11, for each pixel. The primary ray dose estimation process 106 is a process of estimating a primary ray dose in the radiation R, which reaches the irradiation surface 21 of the radiation detector 11, for each pixel. The grid effect estimation process 107 is a process of estimating the effect of improving image quality in a case in which the grid represented by the virtual grid characteristics 101 is used for each pixel.

The scattered ray removal processing unit 100 performs the scattered ray dose estimation process 105 with reference to a first pixel value 108 which is a pixel value of the marker image 40 extracted by the marker image extraction unit 80. The first pixel value 108 is, for example, an average value of the pixel values of all of the pixels constituting the marker image 40. The first pixel value 108 is an example of "a pixel value based on radiation attenuated by a radiation attenuation member" according to the technology of the present disclosure and has only a scattered ray component. In addition, the scattered ray dose estimation process 105 is performed using not only the first pixel value 108 but also various kinds of information including the imaging menu 75 (part of interest), the size of the irradiation field of the radiation R, the irradiation conditions of the radiation R, the thickness of the patient P, the distance from the focus F of the radiation R to the irradiation surface 21 of the radiation detector 11, that is, a source image receptor distance (SID), and the distance between the patient P and the radiation detector 11. The SID and the distance between the patient P and the radiation detector 11 can be derived from, for example, the position of the marker image 40 included in the radiographic image RI and the marker magnification ratio. Alternatively, the SID and the distance between the patient P and the radiation detector 11 may be measured using a distance sensor.

Further, the scattered ray removal processing unit 100 performs the primary ray dose estimation process 106 with reference to a difference 111 between the first pixel value 108 and a second pixel value 110 which is a pixel value of a surrounding region 109 of the marker image 40. The surrounding region 109 is, for example, a region surrounded by a circle, which has the same center as the marker image 40 and has an area that is twice the area of the marker image 40, and is a region excluding the marker image 40. The second pixel value 110 is, for example, an average value of the pixel values of all of the pixels constituting the surrounding region 109. The second pixel value 110 is an example of "a pixel value based on radiation that is not attenuated by the radiation attenuation member" according to the technology of the present disclosure and has a scattered ray component and a primary ray component.

Therefore, the difference 111 between the first pixel value 108 and the second pixel value 110 has only the primary ray component. In addition, the primary ray dose estimation process 106 is also performed using not only the difference 111 but also the above-mentioned various kinds of information, like the scattered ray dose estimation process 105.

The scattered ray removal processing unit 100 corrects an estimated scattered ray dose 112 estimated by the scattered ray dose estimation process 105 and an estimated primary ray dose 113 estimated by the primary ray dose estimation process 106, using the grid effect estimation process 107, to obtain a corrected scattered ray dose 114 and a corrected primary ray dose 115. The scattered ray removal processing unit 100 converts the pixel value of each pixel of the radiographic image RI into a pixel value corresponding to the corrected scattered ray dose 114 and the corrected primary ray dose 115, thereby converting the radiographic image RI into the removed radiographic image RIR.

As described above, in the second embodiment, the scattered ray removal processing unit 100 performs the scattered ray removal process corresponding to the virtual grid characteristics 101 on the radiographic image RI with reference to the first pixel value 108 and the second pixel value 110. Therefore, it is possible to derive the estimated scattered ray dose 112 and the estimated primary ray dose 113 with higher accuracy. As a result, it is possible to perform the scattered ray removal process with higher accuracy.

In a case in which the patient P in the decubitus position is imaged from the side, the thickness of the patient P is thicker than that, for example, in a case in which the patient P in the standing position is imaged from the front. Then, as the thickness of the patient P becomes larger, the scattered ray dose becomes larger. Therefore, in a case in which the patient P in the decubitus position is imaged from the side, it is possible to further exert the effect of performing the scattered ray removal process with higher accuracy.

In addition, the scattered ray removal process of the scattered ray removal processing unit 100 may be performed on the processed radiographic image RIP whose size has been changed according to the correction magnification 93.

Figure 16:
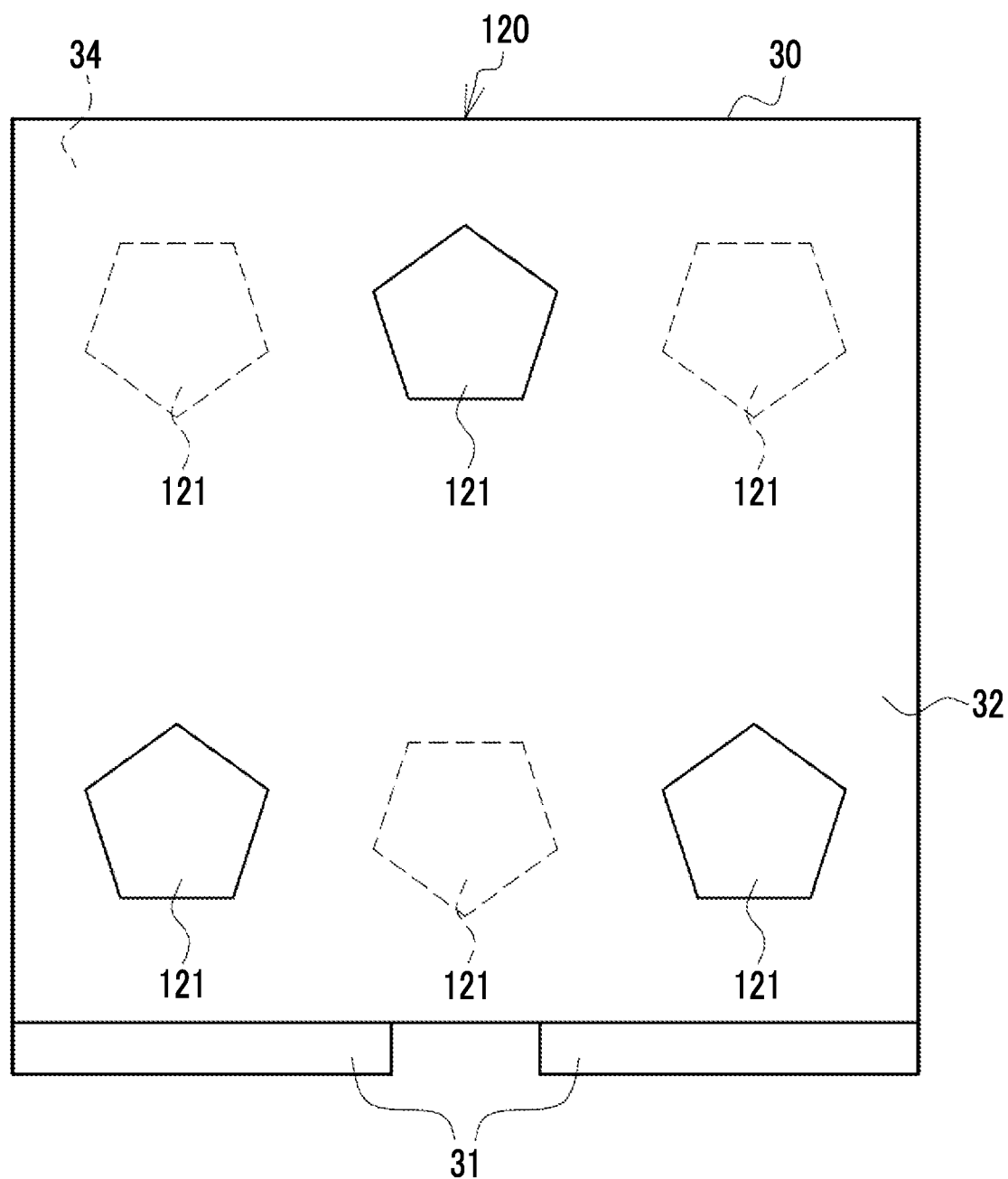
FIG. 16 is a diagram illustrating another example of the marker.

The shape of the lead plate is not limited to the circular shape given as an example. For example, like a marker 120 illustrated in FIG. 16, a lead plate 121 having a regular pentagonal shape may be used. In this case, the directions of the lead plates 121 on the front surface 32 and the rear surface 34 of the main body 30 are 180° different from each other. This makes it easy to extract the marker image.

Figure 17:
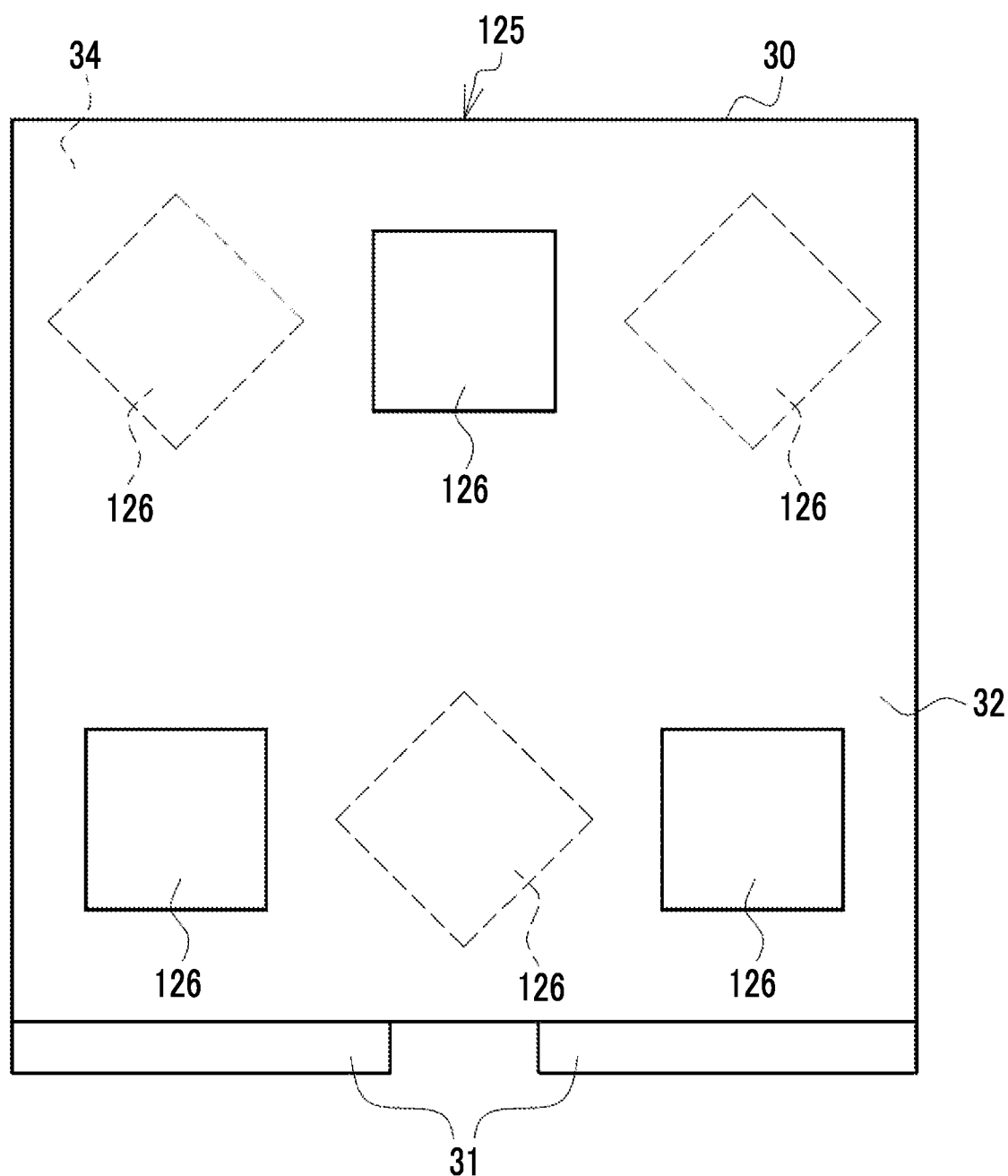
FIG. 17 is a diagram illustrating still another example of the marker.

Further, for example, like a marker 125 illustrated in FIG. 17, a lead plate 126 having a square shape may be used. In this case, the directions of the lead plates 126 on the front surface 32 and the rear surface 34 of the main body 30 is 45° different from each other. This makes it easy to extract the marker image as in the case illustrated in FIG. 16. In addition, the shape of the lead plate may be, for example, a pentagram.

The number of lead plates is not limited to six. For example, the number of lead plates may be two or eight. In addition, the number of lead plates is not limited to two or more. For example, like a marker 130 illustrated in FIG. 18, one lead plate 131 having a circular shape may be attached to the front surface 32. In this case, an actual diameter DM of the lead plate 131 is registered in the actual size information 61. The image processing unit 68 converts the diameter of the marker image 40 in the real space on the basis of the extraction result 90 of the marker images 40. Then, the image processing unit 68 divides the converted diameter of the marker image 40 in the real space by the actual diameter DM of the lead plate 131 registered in the actual size information 61 to calculate the marker magnification ratio.

In the first embodiment, the marker 12 having the main body 30 with a cubic shape is given as an example. However, the present disclosure is not limited thereto. For example, a marker 135 illustrated in FIG. 19 may be used. The marker 135 is composed of a main body 136 and a pedestal 137 that is attached to a bottom of the main body 136. The main body 136 is a rectangular parallelepiped that has a depth LM and a height HM of, for example, 50 mm and a width WM of, for example, 100 mm. Three lead plates 139 having a circular shape are attached to a front surface 138 of the main body 136. Three lead plates 139 having a circular shape are also attached to a rear surface 140 of the main body 136 which is opposite to the front surface 138. The three lead plates 139 are disposed at the vertices of an isosceles triangle on each of the front surface 138 and the rear surface 140. The disposition of the lead plates 139 attached to the front surface 138 and the disposition of the lead plates 139 attached to the rear surface 140 are 180° different from each other.

A plurality of types of markers having different shapes may be used. For example, the marker 12 according to the first embodiment is disposed at the first position PS1, and the marker 135 illustrated in FIG. 19 is disposed at the second position PS2.

The size (for example, the depth LM, the height HM, and the width WM) of the marker, the size (for example, the diameter DM) of the lead plate, and the interval DT between adjacent lead plates are not limited to the numerical values described above as an example.

First, the radiographic image RI whose size has not yet been changed may be displayed on the display 54, the size of the radiographic image RI may be changed according to the correction magnification 93 in response to an instruction from the operator, and the processed radiographic image RIP may be displayed on the display 54.

The radiation source 10 is not limited to the portable radiation source described as an example. The radiation source 10 may be a radiation source that is installed in an imaging room. The patient P is given as an example of the subject. However, the subject may be an animal under treatment such as a horse or a cow.

In each of the above-described embodiments, for example, the following various processors can be used as a hardware structure of processing units performing various processes, such as the receiving unit 65, the detector control unit 66, the acquisition unit 67, the image processing unit 68, the display control unit 69, the marker image extraction unit 80, the interval conversion unit 81, the magnification ratio calculation unit 82, the correction magnification calculation unit 83, and the size change unit 84. The various processors include, for example, the CPU 52 which is a general-purpose processor executing software (operation program 60) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs and/or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As described above, various processing units are configured by one or more of the various processors as a hardware structure.

Furthermore, specifically, an electric circuit (circuitry) obtained by combining circuit elements, such as semiconductor elements, can be used as the hardware structure of the various processors.

In the technology of the present disclosure, the above-described various embodiments and/or various modification examples may be combined with each other. In addition, the present disclosure is not limited to each of the above-described embodiments, and various configurations can be used without departing from the gist of the present disclosure. Furthermore, the technology of the present disclosure extends to a storage medium that non-temporarily stores a program, in addition to the program.

The above descriptions and illustrations are detailed descriptions of portions related to the technology of the present disclosure and are merely examples of the technology of the present disclosure. For example, the above description of the configurations, functions, operations, and effects is the description of examples of the configurations, functions, operations, and effects of portions according to the technology of the present disclosure. Therefore, unnecessary portions may be deleted or new elements may be added or replaced in the above descriptions and illustrations without departing from the gist of the technology of the present disclosure. In addition, the description of, for example, common technical knowledge that does not need to be particularly described to enable the implementation of the technology of the present disclosure are omitted in order to avoid confusion and facilitate the understanding of portions related to the technology of the present disclosure.

In the specification, "A and/or B" is synonymous with "at least one of A or B". That is, "A and/or B" means only A, only B, or a combination of A and B. Further, in the specification, the same concept as "A and/or B" is applied to a case in which the connection of three or more matters is expressed by "and/or".

All of the publications, the patent applications, and the technical standards described in the specification are incorporated by reference herein to the same extent as each individual document, each patent application, and each technical standard are specifically and individually stated to be incorporated by reference.

What is claimed is:

1. An image processing device comprising a processor, wherein the processor acquires a radiographic image which includes a subject and markers including radiation attenuation members and has been captured in a state in which the markers are disposed at a first position between a radiation source and the subject and a second position between a radiation detector and the subject, the subject being interposed between the first and second positions, calculates a correction magnification for setting a part of interest in the subject included in the radiographic image to a set dimension, on the basis of sizes of images of a plurality of the markers included in the radiographic image and an actual size of the markers, and changes a size of the radiographic image according to the correction magnification, and wherein each marker includes a cubic main body formed of a material that transmits the radiation and a pedestal attached to a bottom of the main body, and a plurality of the radiation attenuation members are provided with a predetermined interval at side surfaces of the cubic main body that opposes to each other.

2. The image processing device according to claim 1, wherein the processor acquires the radiographic image captured in a state in which a predetermined positional relationship is established between the first position and a position of the subject and between the second position and the position of the subject.

3. The image processing device according to claim 2, wherein the processor acquires the radiographic image captured in a state in which the first position and the second position are symmetric with respect to a central axis of the subject.

4. The image processing device according to claim 1, wherein the processor acquires the radiographic image captured in a state in which the plurality of markers are disposed at the second positions.

5. The image processing device according to claim 1, wherein the processor calculates the correction magnification on the basis of an interval between images of the radiation attenuation members included in the radiographic image and an actual interval between the radiation attenuation members.

6. The image processing device according to claim 1, wherein the processor performs a scattered ray removal process corresponding to characteristics of a virtual grid on the radiographic image with reference to a pixel value based on radiation, which has been attenuated by the radiation attenuation member, and a pixel value based on radiation, which has not been attenuated by the radiation attenuation member.

7. The image processing device according to claim 1, wherein the processor acquires the radiographic image obtained by imaging the subject in a decubitus position from a side.

8. The image processing device according to claim 1, wherein the processor acquires the radiographic image output from the radiation detector having a size that covers at least half of a body of the subject.

9. The image processing device according to claim 1, wherein the set dimension is an actual size.

10. The image processing device according to claim 1, wherein the part of interest is a spine.

11. A method for operating an image processing device, the method comprising:

acquiring a radiographic image which includes a subject and markers including radiation attenuation members and has been captured in a state in which the markers are disposed at a first position between a radiation source and the subject and a second position between a radiation detector and the subject, the subject being interposed between the first and second positions;

calculating a correction magnification for setting a part of interest in the subject included in the radiographic image to a set dimension, on the basis of sizes of images of a plurality of the markers included in the radiographic image and an actual size of the markers; and changing a size of the radiographic image according to the correction magnification;

wherein each marker includes a cubic main body formed of a material that transmits the radiation and a pedestal attached to a bottom of the main body, and a plurality of the radiation attenuation members are provided with a predetermined interval at side surfaces of the cubic main body that opposes to each other.

12. A non-transitory computer-readable storage medium storing a program for operating an image processing device, the program causing a computer to execute a process comprising:

acquiring a radiographic image which includes a subject and markers including radiation attenuation members and has been captured in a state in which the markers are disposed at a first position between a radiation source and the subject and a second position between a radiation detector and the subject, the subject being interposed between the first and second positions;

calculating a correction magnification for setting a part of interest in the subject included in the radiographic image to a set dimension, on the basis of sizes of images of a plurality of the markers included in the radiographic image and an actual size of the markers; and changing a size of the radiographic image according to the correction magnification;

wherein each marker includes a cubic main body formed of a material that transmits the radiation and a pedestal attached to a bottom of the main body, and a plurality of the radiation attenuation members are provided with a predetermined interval at side surfaces of the cubic main body that opposes to each other.

13. A radiography system comprising:

a radiation source that irradiates a subject with radiation;

a radiation detector that detects the radiation transmitted through the subject and outputs a radiographic image;

markers that include radiation attenuation members and are disposed at a first position between the radiation source and the subject and a second position between the radiation detector and the subject, the first and second positions being included in the radiographic image, the subject being interposed between the first and second positions; and an image processing device that acquires the radiographic image, calculates a correction magnification for setting a part of interest in the subject included in the radiographic image to a set dimension, on the basis of sizes of images of a plurality of the markers included in the radiographic image and an actual size of the markers, and changes a size of the radiographic image according to the correction magnification;

wherein each marker includes a cubic main body formed of a material that transmits the radiation and a pedestal attached to a bottom of the main body, and a plurality of the radiation attenuation members are provided with a predetermined interval at side surfaces of the cubic main body that opposes to each other.

* * * * *